(12) United States Patent
Jemielity et al.

(10) Patent No.: US 8,153,773 B2
(45) Date of Patent: Apr. 10, 2012

(54) SYNTHESIS AND USE OF ANTI-REVERSE PHOSPHOROTHIOATE ANALOGS OF THE MESSENGER RNA CAP

(75) Inventors: Jacek Jemielity, Warsaw (PL); Ewa M. Grudzien-Nogalska, Shreveport, LA (US); Joanna Kowalska, Radom (PL); Edward Darzynkiewicz, Izabelin (PL); Robert E. Rhoads, Shreveport, LA (US)

(73) Assignees: Board of Supervisors of Louisiana State University and Agricultural and Mechanical College, Baton Rouge, LA (US); University of Warsaw, Warsaw (PL)

( * ) Notice: Subject to any disclaimer, the term of this patent is extended or adjusted under 35 U.S.C. 154(b) by 389 days.

(21) Appl. No.: 12/280,282

(22) PCT Filed: Jun. 19, 2008

(86) PCT No.: PCT/US2008/067494
§ 371 (c)(1), (2), (4) Date: Aug. 21, 2008

(87) PCT Pub. No.: WO2008/157688
PCT Pub. Date: Dec. 24, 2008

(65) Prior Publication Data
US 2010/0233757 A1    Sep. 16, 2010

Related U.S. Application Data

(60) Provisional application No. 60/944,842, filed on Jun. 19, 2007.

(51) Int. Cl.
*C07H 21/00* (2006.01)
*C12Q 1/68* (2006.01)
*C12P 19/34* (2006.01)
*A61K 38/00* (2006.01)

(52) U.S. Cl. ...... 536/23.1; 536/24.3; 435/6.1; 435/91.1; 435/91.2; 530/300

(58) Field of Classification Search ............. 435/6, 91.1, 435/91.2; 536/23.1, 24.3; 530/300
See application file for complete search history.

(56) References Cited

U.S. PATENT DOCUMENTS
5,470,967 A * 11/1995 Huie et al. ............ 536/24.3
(Continued)

OTHER PUBLICATIONS

Both, G. et al., "Methylation-dependent translation of viral messenger RNAs in vitro," Proc. Natl. Acad. Sci. USA, vol. 72, pp. 1189-1193 (1975).
(Continued)

*Primary Examiner* — Jezia Riley
(74) *Attorney, Agent, or Firm* — Bonnie J. Davis; John H. Runnels

(57) ABSTRACT

New RNA cap analogs are disclosed containing one or more phosphorothioates groups. The analogs also contain modifications at the 2'-O position of 7-methylguanosine that prevent them from being incorporated in the reverse orientation during in vitro synthesis of mRNA and that hence are "anti-reverse cap analogs" (ARCAs). The ARCA modification ensures that the S atom is precisely positioned within the active sites of cap-binding proteins in both the translational and decapping machinery. The new S-ARCA analogs are resistant to in vivo decapping enzymes. Some S-ARCAs have a higher affinity for eIF4E than the corresponding analogs not containing a phosphorothioate group. When mRNAs containing the various S-ARCAs are introduced into cultured cells, some are translated as much as five-fold more efficiently than mRNAs synthesized with the conventional analog m⁷GpppG.

67 Claims, 10 Drawing Sheets

U.S. PATENT DOCUMENTS

| | | | | |
|---|---|---|---|---|
| 5,643,780 | A | * | 7/1997 | Baker .......................... 435/375 |
| 7,074,596 | B2 | | 7/2006 | Darzynkiewicz et al. ...... 435/90 |
| 2005/0227331 | A1 | | 10/2005 | Breaker .......................... 435/85 |
| 2006/0252115 | A1 | | 11/2006 | Darzynkiewicz et al. ... 435/68.1 |

OTHER PUBLICATIONS

Burgers, P. et al., "Absolute Configuration of the Diastereomers of Adenosine 5'-O-(1-thiotriphosphate): Consequences for the stereochemistry of polymerization by DNA-dependent RNA polymerase from *Escherichia coli*", Proc. Natl. Acad. Sci. U.S.A., vol. 75, pp. 4798-4800 (1978).

Cassel, D. et al., "Activation of turkey erythrocyte adenylate cyclase and blocking of the catecholamine-stimulated GTPase by guanosine 5'-(gamma-thio) triphosphate", Biochem Biophys Res Commun, vol. 77, pp. 868-873 (1977).

Chu, L. et al., "Paradoxical observations on the 5' terminus of ovalbumin messenger ribonucleic acid," J. Biol. Chem., vol. 253, pp. 5228-5231 (1978).

Contreras, R. et al., "Simple, efficient in vitro synthesis of capped RNA useful for direct expression of cloned eukaryotic genes," Nucl. Acids Res., vol. 10, pp. 6353-6362 (1982).

Darzynkiewicz, E. et al., "β-Globin mRNAs capped with m7G, m22. 7G or m32.2.7G differ in intrinsic translation efficiency," Nucl. Acids Res., vol. 16, pp. 8953-8962 (1988).

Darzynkiewicz, E. et al., "Inhibition of eukaryotic translation by nucleoside 5'-monophosphate analogues of mRNA 5'-cap: Changes in N7 substituent affect analogue activity," Biochem., vol. 28, pp. 4771-4778 (1989).

Darzynkiewicz, E. et al., "Methylene and phosphorothioate cap dinucleotides: useful tools to study decapping and translantion", an abstract and poster presented to the RNA Meeting, Seattle, Washington, Jun. 20-25, 2006.

Eckstein, F. et al., "Guanosine 5'-O-(2-thiodiphosphate). An inhibitor of adenylate cyclase stimulation by guanine nucleotides and fluoride ions", J. Biol. Chem., vol. 254, pp. 9829-9834 (1979).

Eckstein, F. et al., "Stereochemistry of the transesterification step of ribonuclease T 1", Biochemistry, vol. 11, pp. 3507-3512 (1972).

Edery, I. et al., "Cap-dependent RNA splicing in a HeLa nuclear extract," Proc. Natl. Acad. Sci. USA, vol. 82, pp. 7590-7594 (1985).

Grudzien, E. et al., "Differential inhibition of mRNA degradation pathways by novel cap analogs," J. Biol. Chem. vol. 281, pp. 1857-1867 (2006).

Grudzien, E. et al., "Novel cap analogs for in vitro synthesis of mRNAs with high translational efficiency," RNA vol. 10, pp. 1479-1487 (2004).

Grudzien-Nogalska, E. et al., "Phosphorothioate cap analogs stabilize mRNA and increase translational efficiency in mammalian cells," RNA, vol. 13, No. 10, pp. 1745-1755 (2007).

Jemielity, J. et al. "Novel 'anti-reverse' cap analogues with superior translational properties," RNA, vol. 9, pp. 1108-1122 (2003).

Konarska, M. et al., Recognition of cap structure in splicing in vitro of mRNA precursors. Cell, vol. 38, pp. 731-736 (1984).

Kowalska, J. et al., "Synthesis and characterization of mRNA cap analogs containing phosphorothioate substitutions that bind tightly to eIF4E and are resistant to the decapping pyrophosphatase DcpS," RNA, vol. 14, pp. 1119-1131 (2008).

Kowalska, J. et al. "Synthesis and properties of mRNA cap analogs containing phosphorothioate moiety in 5',5'-triphosphate chain," Nucleos. Nucleot. Nucl. Acids, vol. 24, pp. 595-600 (2005).

Matsukura, M. et al., "Phosphorothioate analogs of oligodeoxynucleotides: Inhibitors of replication and cytopathic effects of human immunodeficiency virus," Proc. Natl. Acad. Sci., vol. 84, pp. 7706-7710 (1987).

Matzura, H. et al., "A polyribonucleotide containing alternation P=O and P=S linkages", Eur. J. Biochem., vol. 3, pp. 448-452 (1968).

Melton, D. et al., "Efficient in vitro synthesis of biologically active RNA and RNA hybridization probes from plasmids containing a bacteriophage SP6 promoter," Nucl. Acids Res., vol. 12, pp. 7035-7056 (1984).

Muthukrishnan, S. et al., "5'-Terminal 7-methylguanosine in eukaryotic mRNA is required for translation," Nature, vol. 255, pp. 33-37 (1975).

Pasquinelli, A. et al., "Reverse 5' caps in RNAs made in vitro by phage RNA polymerases," RNA, vol. 1, pp. 957-967 (1995).

Peng, Z. et al., "Synthesis and application of a chain-terminating dinucleotide mRNA cap analog," Org. Lett., vol. 4, pp. 161-164 (2002).

Potter, B. et al., "Synthesis and configurational analysis of a dinucleoside phosphate isotopically chiral at phosphorus. Stereochemical course of Penicillium citrum nuclease P1 reaction.", Biochemistry, vol. 22, pp. 1369-1377 (1983).

Stepinski, J. et al., "Synthesis and properties of mRNAs containing the novel 'anti-reverse' cap analogues 7-methyl(3'-O-methyl)GpppG and 7-methyl(3'-deoxy)GpppG," RNA, vol. 7, pp. 1486-1495 (2001).

Wang, Z. et al., "The hDcp2 protein is a mammalian mRNA decapping enzyme," Proc. Natl. Acad. Sci. U.S.A., vol. 99, pp. 12663-12668 (2002).

Wieczorek, Zbigniew et al., "Fluorescence and NMR Studies of Intramolecular Stacking of mRNA Cap-analogues," Biochimca et Biophyica Acta, vol. 1354, pp. 145-152 (1997).

Yisraeli, J. et al., Synthesis of long, capped transcripts in vitro by SP6 and T7 RNA polymerases, pp. 42-50 in J. Dahlberg et al. (Eds.), Meth. Enzymol., vol. 180., pp. 42-50 (1989).

Eckstein, Fritz, "Phosphorothioate Oligodeoxynucleotides: What is Their Origin and What is Unique About Them?" Antisense & Nucleic Acid Drug Dev., vol. 10, pp. 117-121 (2000).

Darzynkiewicz, Z.M. et al., "Interaction of Human Decapping Scavenger with 5' mRNA Cap Analogues: Structural Requirements for Catalytic Activity," J. Phys.: Condensed Matter, vol. 19, no. 28, p. 285217-285222 (2007).

Kowalska, Joanna et al., "Phosphorothioate Analogues of mRNA with Superior Biological Properties," Collection Symposium Series, vol. 10, pp. 362-365 (2008).

\* cited by examiner

SYNTHESIS AND USE OF ANTI-REVERSE PHOSPHOROTHIOATE ANALOGS OF THE MESSENGER RNA CAP

This is the United States national stage of international application PCT/US2008/067494, international filing date 19 Jun. 2008, which claims the benefit of the filing date of provisional U.S. application Ser. No. 60/944,842 filed 19 Jun. 2007, under 35 U.S.C. §119(e).

The development of this invention was partially funded by the Government of Poland under grant number 2 P04A 006 28 awarded by the Polish Ministry of Science and Higher Education.

The development of this invention was partially funded by the United States Government under grant number R01GM20818 awarded by the National Institute of General Medical Sciences. The United States Government has certain rights in this invention.

TECHNICAL FIELD

New anti-reverse phosphorothioate analogs of messenger RNA cap have been synthesized and shown to be useful in translation of mRNA.

BACKGROUND ART

In eukaryotes, the 5' ends of most messenger RNAs (mRNAs) are blocked, or "capped." In addition, there are some other forms of RNA that are also capped, for instance small nuclear RNAs (snRNAs). The cap contains a 5'-5' triphosphate linkage between two nucleoside moieties and a 7-methyl group on a distal guanine ring. The capping of mRNA and snRNA promotes their normal functions in cells.

The ability to synthesize capped RNA molecules in vitro is useful, because it allows workers to prepare RNA molecules that behave properly in a variety of biological applications. Such applications include both research applications and commercial production of polypeptides, e.g., the production in a cell-free translation system of polypeptides containing an "unnatural" amino acid at a specific site, or production in cultured cells of polypeptides that require post-translational modification for their activity or stability. In the latter systems, synthesis proceeds for a considerably longer time and therefore produces more protein.

The method most frequently used to make capped RNAs in vitro is to transcribe a DNA template with either a bacterial or bacteriophage RNA polymerase in the presence of all four ribonucleoside triphosphates and a cap dinucleotide such as m$^7$G(5')ppp(5')G (henceforth m$^7$GpppG). The polymerase initiates transcription with a nucleophilic attack by the 3'-OH of the Guo moiety of m$^7$GpppG on the α-phosphate of the next templated nucleoside triphosphate, resulting in the initial product m$^7$GpppGpN. The alternative, GTP-initiated product pppGpN is suppressed by setting the ratio of m$^7$GpppG to GTP between 5 and 10 in the transcription reaction mixture.

Synthetic RNAs may be synthesized by cell-free transcription of DNA templates. See R. Contreras et al., "Simple, efficient in vitro synthesis of capped RNA useful for direct expression of cloned eukaryotic genes," Nucl. Acids Res., vol. 10, pp. 6353-6362 (1982); J. Yisraeli et al., "Synthesis of long, capped transcripts in vitro by SP6 and T7 RNA polymerases, pp. 42-50 in J. Dahlberg et al. (Eds.), Meth. Enzymol., vol. 180., pp. 42-50 (1989); and D. Melton et al., "Efficient in vitro synthesis of biologically active RNA and RNA hybridization probes from plasmids containing a bacteriophage SP6 promoter," Nucl. Acids Res., vol. 12, pp. 7035-7056 (1984).

Capped RNAs thus produced are active in splicing reactions carried out in vitro. See M. Konarska et al., "Recognition of cap structure in splicing in vitro of mRNA precursors. Cell, vol. 38, pp. 731-736 (1984); and I. Edery et al., "Cap-dependent RNA splicing in a HeLa nuclear extract," Proc. Natl. Acad. Sci. USA, vol. 82, pp. 7590-7594 (1985).

Capped mRNAs are translated in cell-free translation systems more efficiently than are non-capped mRNAs. See S. Muthukrishnan et al., "5'-Terminal 7-methylguanosine in eukaryotic mRNA is required for translation," Nature, vol. 255, pp. 33-37 (1975); L. Chu et al., "Paradoxical observations on the 5' terminus of ovalbumin messenger ribonucleic acid," J. Biol. Chem., vol. 253, pp. 5228-5231 (1978); E. Darzynkiewicz et al., β-Globin mRNAs capped with m$^7$G, m$_2^{2,7}$G or M$_3^{2,2,7}$G differ in intrinsic translation efficiency," Nucl. Acids Res., vol. 16, pp. 8953-8962 (1988); and E. Darzynkiewicz et al., "Inhibition of eukaryotic translation by nucleoside 5'-monophosphate analogues of mRNA 5'-cap: Changes in N7 substituent affect analogue activity," Biochem., vol. 28, pp. 4771-4778 (1989).

5'-Unmethylated mRNAs are translationally less active than 5'-methylated mRNAs. See G. Both et al., "Methylation-dependent translation of viral messenger RNAs in vitro," Proc. Natl. Acad. Sci. USA, vol. 72, pp. 1189-1193 (1975).

Capped mRNAs introduced into cultured mammalian cells by electroporation are translated more efficiently than are non-capped mRNAs. See E. Grudzien et al., "Differential inhibition of mRNA degradation pathways by novel cap analogs," J. Biol. Chem. vol. 281, pp. 1857-1867 (2006).

A. Pasquinelli et al., "Reverse 5' caps in RNAs made in vitro by phage RNA polymerases," RNA, vol. 1, pp. 957-967 (1995), reported that bacteriophage polymerases use the 3'-OH of the 7-methylguanosine moiety of m$^7$GpppG to initiate transcription, demonstrating that approximately one-third to one-half of RNA products made with this cap analogue actually contain the cap in reversed orientation, i.e., Gpppm$^7$GpN. Such reverse-capped RNA molecules behave abnormally. The same authors reported that when reverse-capped pre-U1 snRNA transcripts were injected into Xenopus laevis nuclei, they were exported more slowly than natural transcripts. Similarly, cytoplasmic reverse-capped U1 snRNAs in the cytoplasm were not properly imported into the nucleus.

The presence of a cap on mRNA strongly stimulates translation of an mRNA transcript into protein. E. Grudzien et al., "Novel cap analogs for in vitro synthesis of mRNAs with high translational efficiency," RNA vol. 10, pp. 1479-1487 (2004), demonstrated that mRNAs containing caps incorporated exclusively in the reverse orientation were translated in a cell-free system with only 4% the efficiency of mRNAs containing caps incorporated exclusively in the normal orientation.

J. Stepinski et al., "Synthesis and properties of mRNAs containing the novel 'anti-reverse' cap analogues 7-methyl (3'-O-methyl)GpppG and 7-methyl(3'-deoxy)GpppG," RNA, vol. 7, pp. 1486-1495 (2001) reported the synthesis and use of two novel two novel cap analogs, m$^7$3' dGpppG and m$_2^{7,3'-O}$GpppG, that are incapable of being incorporated in the reverse orientation. mRNAs capped with these "anti-reverse cap analogs" (ARCAs) were translated more efficiently in an in vitro system than mRNAs capped with the conventional analog, m$^7$GpppG. See also U.S. Pat. No. 7,074,596, and U.S. Patent Application Publication 2003/0194759.

Z. Peng et al., "Synthesis and application of a chain-terminating dinucleotide mRNA cap analog," *Org. Lett.*, vol. 4, pp. 161-164 (2002) reported the synthesis of $m_2^{7,3'-O}$GpppG and its use in the in vitro transcription of homogeneously capped RNA.

J. Jemielity et al. "Novel 'anti-reverse' cap analogues with superior translational properties," *RNA*, vol. 9, pp. 1108-1122 (2003) reported that substitution at the 2' position with either —OCH$_3$ or —H, to produce $m_2^{7,2'-O}$GpppG or $m^7$2' dGpppG, respectively, yielded ARCAs with properties equivalent to or slightly more favorable than those of ARCAs substituted at the 3' position as measured by the criteria of binding to the translational cap-binding protein eIF4E, correct incorporation into mRNA during in vitro transcription, and translational efficiency of the resulting mRNAs in a cell-free system.

The amount of protein produced from synthetic mRNAs introduced into cultured mammalian cells is limited by the degradation of mRNA by natural turnover processes. A major in vivo pathway of mRNA degradation is initiated by removal of the cap from intact mRNA by a specific pyrophosphatase, Dcp1/Dcp2, that cleaves between the α and β phosphates. E. Grudzien et al. "Differential inhibition of mRNA degradation pathways by novel cap analogs," *J. Biol. Chem.*, vol. 281, pp. 1857-1867 (2006) designed and synthesized a cap analog in which a methylene group replaced the O atom between α and β phosphate groups, $m_2^{7,3'-O}$Gpp$_{CH2}$pG, mRNAs capped with this analog were resistant to hydrolysis by recombinant human Dcp2 in vitro. When introduced into cultured cells, mRNAs capped with $m_2^{7,3'-O}$Gpp$_{CH2}$pG were more stable than those capped with $m_2^{7,3'-O}$GpppG.

There are two known decapping enzymes: Dcp1/Dcp2, which acts on intact mRNA to initiate 5'→3' degradation; and DcpS, which acts on short capped oligonucleotides resulting from 3'→5' degradation. Because Dcp1/Dcp2 or Dcp2 alone releases m$^7$GDP from capped mRNAs, cleavage is likely to occur between the α- and β-phosphates. See Z. Wang et al., "The hDcp2 protein is a mammalian mRNA decapping enzyme," *Proc. Natl. Acad. Sci. U.S.A.*, vol. 99, pp. 12663-12668 (2002). Previously, it was shown that nucleoside 5'-monophosphorothioates as well as triphosphate analogs such as ATPγS, GTPγS, and GDPβS were stable towards phosphatases. See F. Eckstein et al., "Guanosine 5'-O-(2-thiodiphosphate). An inhibitor of adenylate cyclase stimulation by guanine nucleotides and fluoride ions", *J. Biol. Chem.*, vol. 254, pp. 9829-9834 (1979), and D. Cassel et al., "Activation of turkey erythrocyte adenylate cyclase and blocking of the catecholamine-stimulated GTPase by guanosine 5'-(gamma-thio) triphosphate", *Biochem Biophys Res Commun*, vol. 77, pp. 868-873 (1977). Additionally, polynucleotides containing phosphorothioate internucleotide linkages were found to be degraded more slowly than their natural counterparts. See H. Matzura et al., "A polyribonucleotide containing alternation P═O and P═S linkages", *Eur. J. Biochem.*, vol. 3, pp. 448-452 (1968). Interestingly, the diastereomers of phosphorothioates can exhibit different sensitivities toward nucleases. Nuclease P1 hydrolyses the Sp diastereomer more rapidly than the Rp. See B. Potter et al., "Synthesis and configurational analysis of a dinucleoside phosphate isotopically chiral at phosphorus. Stereochemical course of *Penicillium citrum* nuclease P1 reaction.", *Biochemistry*, vol. 22, pp. 1369-1377 (1983). Ribonuclease T1 and snake venom phosphodiesterase preferably cleave the Rp diastereomer over the Sp. See F. Eckstein et al., "Stereochemistry of the transesterification step of ribonuclease T 1", *Biochemistry*, vol. 11, pp. 3507-3512 (1972), and P. Burgers et al., "Absolute Configuration of the Diastereomers of Adenosine 5'-O-(1-thiotriphosphate): Consequences for the stereochemistry of polymerization by DNA-dependent RNA polymerase from *Escherichia coli*", *Proc. Natl. Acad. Sci. U.S.A.*, vol. 75, pp. 4798-4800 (1978).

Although mRNA capped with $m_2^{7,3'-O}$Gpp$_{CH2}$pG was more stable in cultured cells, it had lower translational efficiency, presumably because $m_2^{7,3'-O}$Gpp$_{CH2}$pG bound to eIF4E in vitro with considerably lower affinity than $m_2^{7,3'-O}$GpppG. Thus, even though it was more stable in cultured cells, this advantage was offset by lower translational efficiency.

J. Kowalska et al. "Synthesis and properties of mRNA cap analogs containing phosphorothioate moiety in 5',5'-triphosphate chain," *Nucleos. Nucleot. Nucl. Acids*, vol. 24, pp. 595-600 (2005) reported synthesis of three cap analogs in which S is substituted for O in either the α, β, or γ phosphate moieties, e.g., m$^7$Gp$_s$ppG, m$^7$Gppp$_s$G and m$^7$Gpp$_{S-CH3}$pG. These synthesized phosphorothioate cap analogs were more stable inhibitors of cap-dependent translation, and were resistant to DcpS decapping enzyme. However, these compounds would not show higher translational efficiency neither in vitro nor in vivo than regular ARCAs, because they would be incorporated to a large extent in the reverse orientation.

There is a need for a modification that would achieve both higher translation efficiency and increase resistance to both in vivo and in vitro degradation. The unique compounds reported here do both.

DISCLOSURE OF INVENTION

We have discovered that S-substitution at one or more phosphates together with 2'-O methyl substitution produces new analogs, called S-ARCAs with surprising properties. The novel ARCA modification ensures that the α, β, and γ phosphorothioate groups are precisely positioned within the active sites of cap-binding proteins in both the translational and decapping machinery. At least some of these analogs are resistant to Dcp1/Dcp2. Some S-ARCAs have a much higher affinity for eIF4E than the corresponding analogs lacking a phosphorothioate group. When mRNAs containing the various S-ARCAs were introduced into cultured cells, some were translated as much as five-fold more efficiently than mRNAs synthesized with the conventional analog, m$^7$GpppG. Furthermore, the half-life of mRNAs capped with some S-ARCAs was as much as three-fold longer than those of mRNAs synthesized with unmodified caps. The combination of a more efficiently translated mRNA and a more stable mRNA resulted in higher overall production of reporter proteins in transfected cells than with conventional synthetic mRNAs or mRNAs capped with earlier ARCAs. The S-ARCAs increased stability in vivo and surprisingly increased the translation efficiency arising from higher affinity to eIF4E combined with Dcp1/Dcp2 resistance. The resistance to hydrolysis by Dcp2 under physiological conditions was surprisingly correlated with a β-phosphorothioate group in triphosphates, and is expected also to correlate with a γ-phosphorothioate in tetraphosphates. Another advantage over regular ARCAs is the occurrence of P-diastereomerism, due to the phosphorothioate moieties. In each case when the phosphorothioate moiety is precisely positioned in α-, β- or γ-positions, there are still two possibilities to place the sulfur atom (proR and proS), that result in two different diastereomers with potentially different biological activity. For example, there were significant differences in binding affinities for eIF4E between counterpart D1 and D2 diastereomers and also mRNA capped with $m_2^{7,2'-O}$Gpp$_s$pG (D1), and this D1 was much more susceptible to Dcp2 than its D2 counterpart]. Hence, diastereomerically pure S-ARCAs may be exploited as P-chiral probes useful for investigation the stereochemical courses of enzymatic processes involving cap.

MODES FOR CARRYING OUT THE INVENTION

Materials and Methods

EXAMPLE 1

General Chemical Procedures

Figure 1:
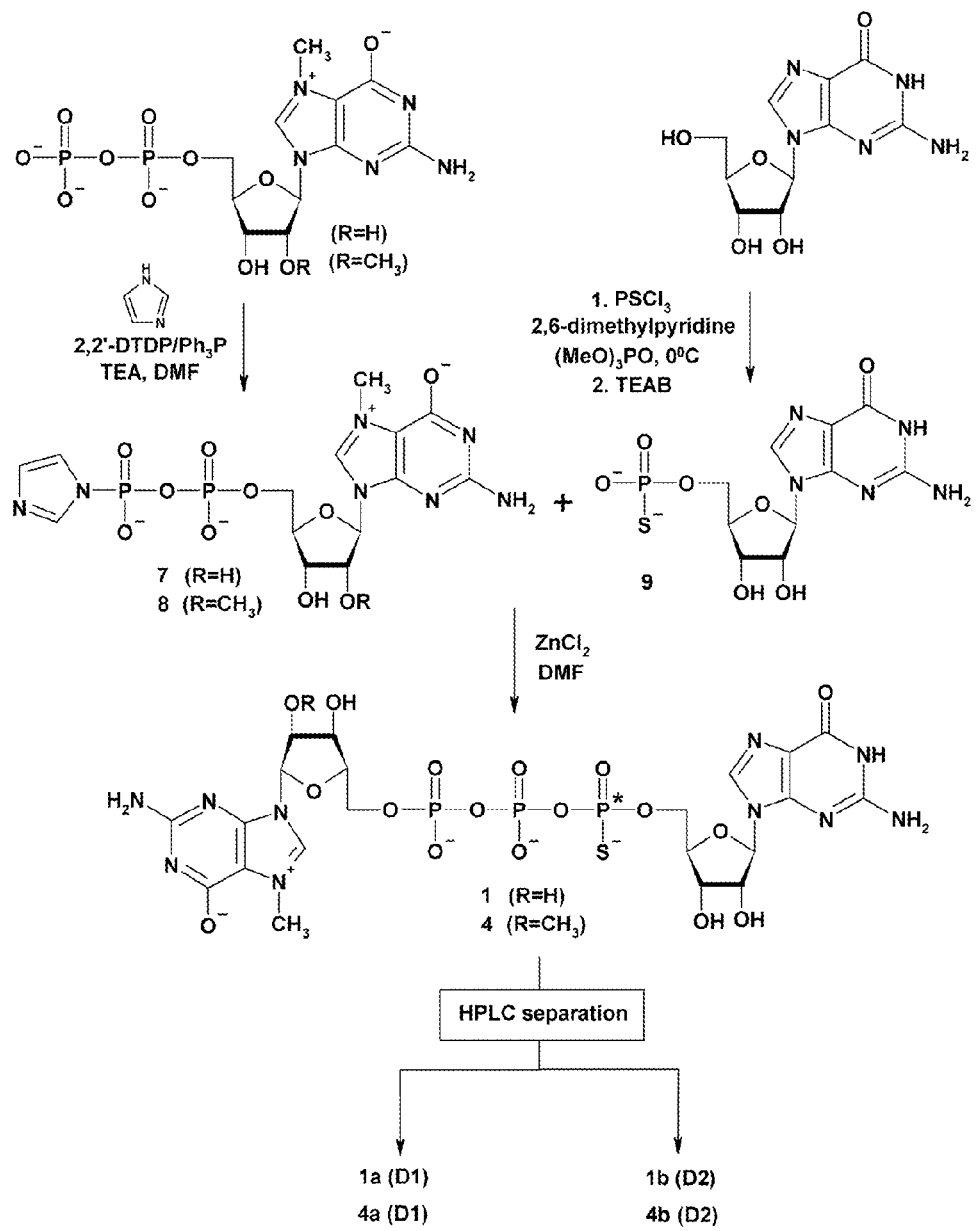
FIG. 1 depicts the synthesis of the α S-ARCA $m_2^{7,2'-O}Gppp_sG$ (D1 and D2).

Intermediate nucleotides were separated by ion-exchange chromatography on a DEAD-Sephadex A-25 ($HCO_3^-$ form) column using a linear gradient of triethylammonium bicarbonate (TEAB) in deionized water, and after evaporation under reduced pressure with addition of ethanol, were isolated as triethylammonium salts. Final products (cap analogs) were separated by either analytical or semipreparative RP HPLC and, after repeated freeze-drying, were isolated as ammonium salts. Analytical HPLC was performed on a Spectra-Physics SP8800 apparatus equipped with a Supelcosil LC-18-T reverse-phase column (4.6×250 mm, flow rate 1.3 ml/min) with a linear gradient 0-25% of methanol in 0.05 M ammonium acetate buffer at pH 5.9, using UV-detection at 260 nm. Semi-preparative HPLC was performed on a Waters 600E Multisolvent Delivery System equipped with a Waters HR-C-18 reverse-phase column (19×300 mm, flow rate 5.0 m/min) with a linear gradient of methanol in 0.05 M ammonium acetate buffer, pH 5.9, using UV-detection at 260 nm.

GMP and GDP were purchased from Sigma-Aldrich and converted into triethylammonium salts using Dowex 50 WX 8 ion-exchange resin. Other nucleotides, i.e. $m^7GMP$, $m_2^{7,2'-O}GMP$, $m^7GDP$, $m_2^{7,2'-O}GDP$ were prepared as previously reported in J. Jemielity et al. "Novel 'anti-reverse' cap analogues with superior translational properties," RNA, vol. 9, pp. 1108-1122 (2003). Thiophosphate triethylammonium salt was prepared from $Na_3PSO_3$ by conversion on Dowex 50 WX 8 ion-exchange resin and (after evaporation to dryness) and re-evaporation with 99.8% ethanol stored at −20° C. See J Kowalska et al. "A simple and rapid synthesis of nucleotide analogues containing a phosphorothioate moiety at the terminal position of the phosphate chain", Tetrahedron Lett., vo. 48, pp. 5475-5479 (2007). 7-methylguanosine was prepared as previously reported, with the exception that DMF was used instead of DMA (See J. Jones et al., "Purine Nucleosides. 111. Methylation Studies of Certain Naturally Occurring Purine Nucleosides", J. Am. Chem. Soc., vol. 85, pp. 193-201 (1963). 7,2'-O-dimethylguanosine was synthesized from 2'-O-methylguanosine by an analogous procedure. 2'-O-methylguanosine was prepared according to J. Kusmierek et al., "A new route to 2'(3')—O-alkyl purine nucleosides", Nucleic Acids Res. vol. 1, pp, 73-77, Special Publication No. 4 (1978).

The structure and homogeneity of the final compounds was confirmed by re-chromatography on RP HPLC, mass spectrometry using negative electrospray ionization (MS ESI-) and $^1H$ NMR and $^{31}P$ NMR spectroscopy. (Results are shown in Table 1)$^1H$ NMR and $^{31}P$ NMR spectra were recorded at 25° C. on a Varian UNITY-plus spectrometer at 399.94 MHz and 161.90 MHz respectively. $^1H$ NMR chemical shifts were reported to sodium 3-trimethylsilyl-[2,2,3,3-D4]-propionate (TSP) in $D_2O$ as an internal standard. $^{31}P$ NMR chemical shifts were reported to 20% phosphorus acid in $D_2O$ as an external standard. Mass spectra were recorded on a Micromass QToF 1 MS spectrometer using negative electrospray ionization (ESI-).

EXAMPLE 2

General Procedure for Nucleotide Imidazolide Derivatives (GMP-Im, $m_2^{7,2'-O}GMP$-Im, GDP-Im, and $m_2^{7,2'-O}GDP$-Im) (7, 8, and 12-15)

See T. Mukaiyama, et al. "Phosphorylation by oxidation-reduction condensation. Preparation of active phosphorylating reagents", M. Bull. Chem. Soc. Jpn, vol. 44, 2284 (1971). An appropriate nucleotide (1 eq. TEA salt), imidazole (8 eq.), and 2,2'-dithiodipyridine (3 eq.) were mixed in DMF (approx. 2.5 ml/100 mg of nucleotide). Triethylamine (2 eq.) and triphenylphosphine (3 eq.) were added, and the mixture was stirred for 6-8 h. The product was precipitated from the reaction mixture with anhydrous sodium perchlorate (1 eq. per one negative charge) dissolved in dry acetone (approx. 8 ml/1 ml of DMF). After cooling to 4° C. the precipitate was filtered, washed repeatedly with cold, dry acetone, and dried in vacuum over $P_4O_{10}$. Yields were 80-100%. In case of $m^7GMP$, due to its lower solubility in DMF, 2-fold larger excess of reagents was used, and reaction time was extended to 24 h.

EXAMPLE 3

General Procedure for Nucleoside 5'-O-phosphorothioates (9-11)

A suspension of an appropriate nucleoside (1 eq, dried overnight in vacuum over $P_4O_{10}$) in trimethyl phosphate (1.5 ml/100 mg of nucleoside) was cooled to 0° C. on ice/water bath. 2,6-dimethylpyridine (3 eq.) and $PSCl_3$ (1.5 eq.) were added. The reaction was maintained at 0° C. overnight, then quenched with 0.35 M TEAB and stirred for 1 h at RT. The product was separated by DEAE Sephadex chromatography using a linear gradient of 0-0.7 M TEAB. Yields: (9) 380 mg (0.67 mmol) starting from 257 mg (0.91 mmol) of guanosine (74%); (10) 57 mg (0.10 mmol) starting from 120 mg (0.42 mmol) of 7-methylguanosine (24%); (11) 75 mg (0.13 mmol) starting from 70 mg (0.23 mmol) of 7,2'-O-dimethylguanosine (53%).

EXAMPLE 4

Synthesis of Nucleoside 5'-(2-O-thiodiphosphates)

7,2'-O-dimethylguanosine 5'-O-(2-thiodiphosphate) (17). To a suspension of 14 (100 mg, 0.21 mmol) and thiophosphate triethylammonium salt (220 mg) in 5 ml of DMF anhydrous $ZnCl_2$ (190 mg, 1.40 mmol) was added. The resulting solution was stirred for 20 min at RT. The reaction was quenched by addition of solution of EDTA (520 mg, 1.40 mmol) in 50 ml of water and neutralized with solid $NaHCO_3$. The product was isolated on DEAE Sephadex using 0-1.0 M gradient of TEAB. Yield: 106 mg (0.15 mmol) of (17) as TEA salt (71%).

7-methylguanosine 5'-O-(2-thiodiphosphate) (16). This compound was synthesized as described for (17) starting from (13) (40 mg, 0.089 mmol) and thiophosphate triethylammonium salt (100 mg). Yield: 31 mg (0.046 mmol) of (16) as TEA salt (52%).

EXAMPLE 5

Synthesis of Cap S-ARCAs

Figure 2:
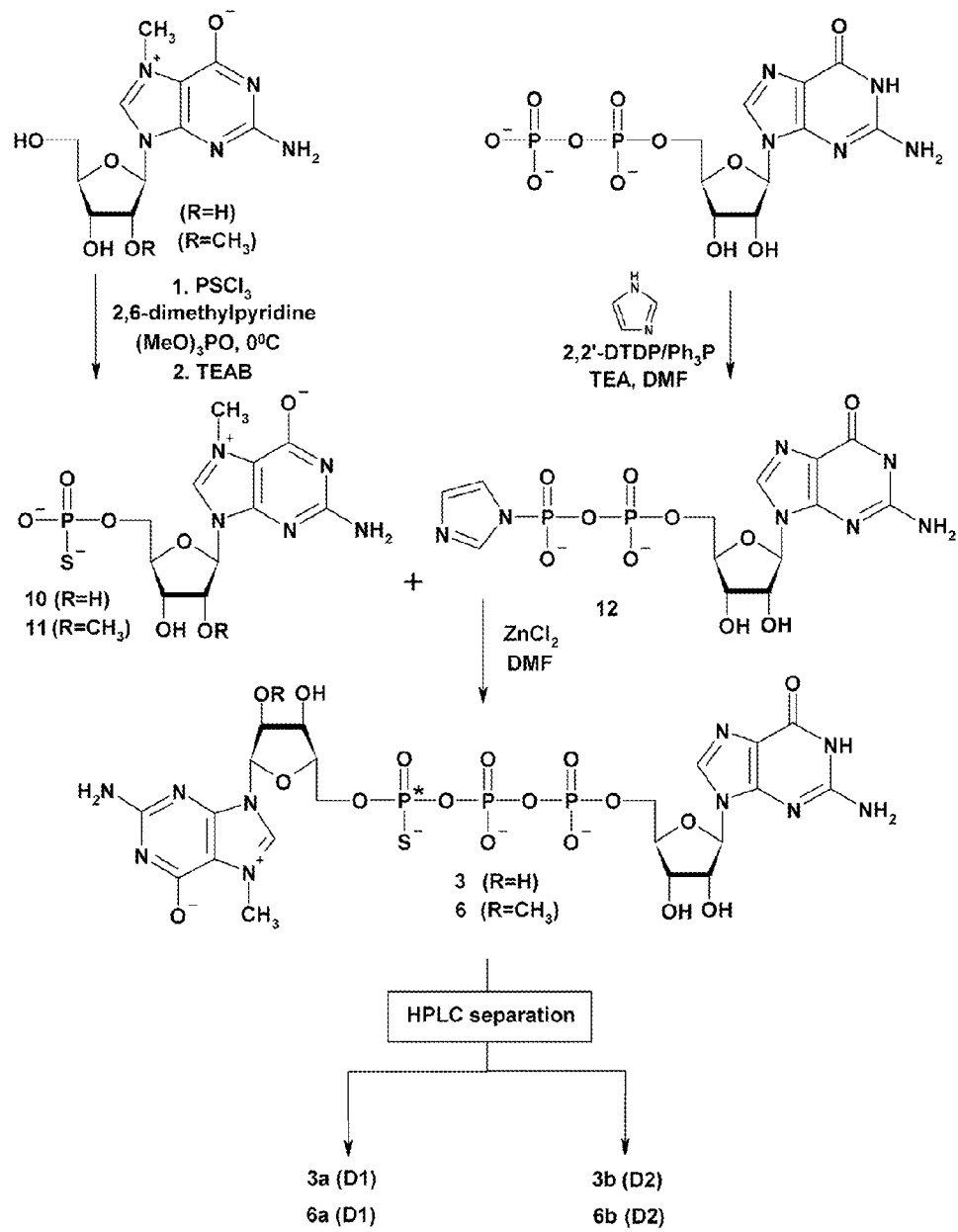
FIG. 2 depicts the synthesis of the γ S-ARCA $m_2^{7,2'-O}Gp_sppG$ (D1 and D2).
Figure 3:
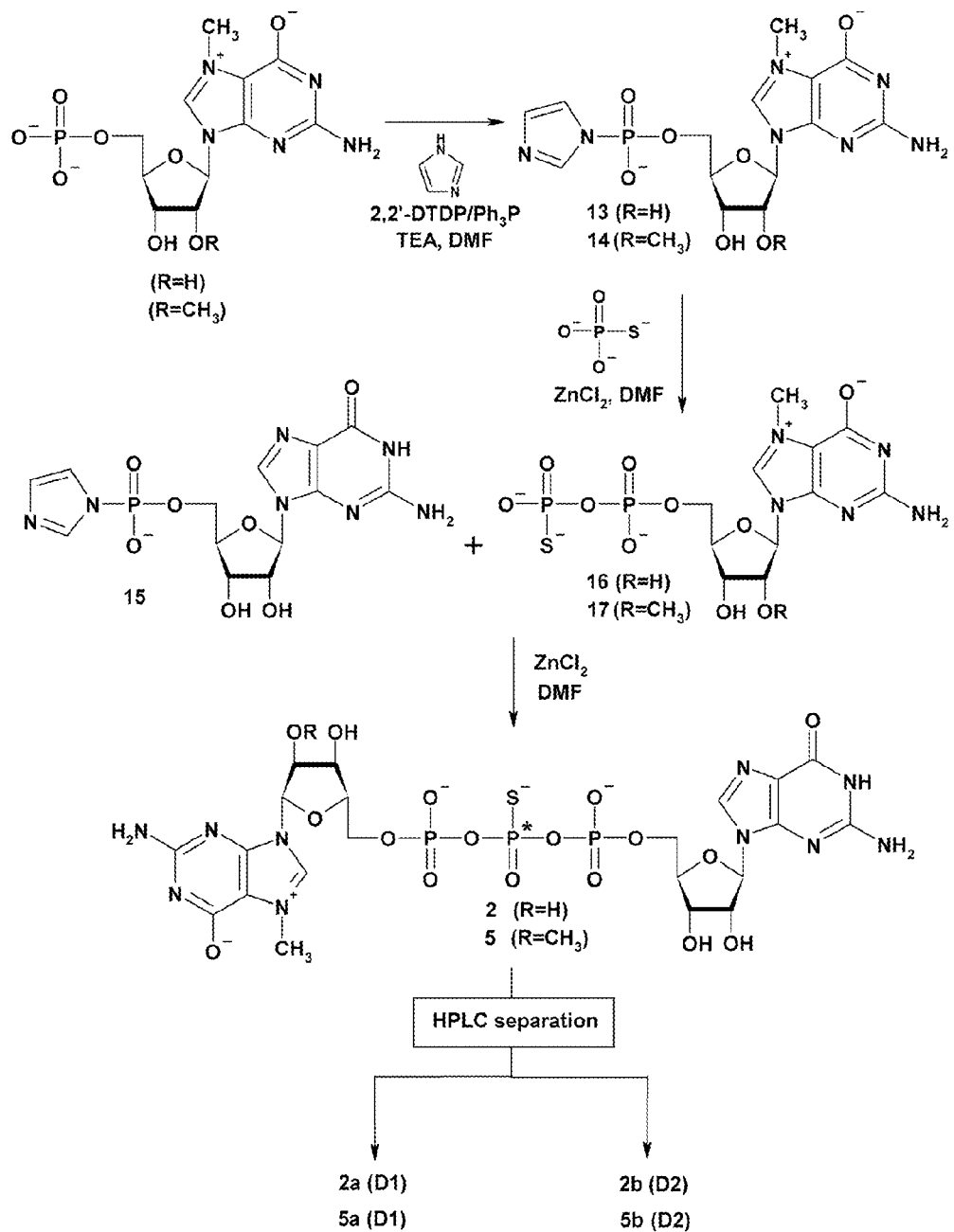
FIG. 3 depicts the synthesis of the β S-ARCA $m_2^{7,2'-O}Gpp_sG$ (D1 and D2).

Below are the descriptions for the synthesis of various cap S-ARCAs. The synthesis pathways are depicted in FIGS. 1, 2, and 3. The (numbers) refer to compounds as numbered in FIGS. 1, 2, and 3.

$m^7Gppp_sG$ D1 and D2 (1a, 1b). To a suspension of (9) (10 mg, 0.018 mmol) and 7 (15 mg, 0.027 mmol) in DMF (0.8 ml) anhydrous $ZnCl_2$ (30 mg, 0.22 mmol) was added. The reaction was maintained at RT for 2 days. The reaction was quenched by addition of 90 mg of EDTA in 10 ml of water and neutralized with solid $NaHCO_3$. The diastereomers (1a) and (1b) were separated by analytical RP HPLC. Yield: 0.8 mg of (1a) and 1.0 mg of (1b) as $NH_4^+$ salts. A schematic of the synthesis is shown if FIG. 1.

$m^7Gpp_spG$ D1 and D2 (2a, 2b). This compound was synthesized as described for 1-starting from 16 (20 mg, 0.030 mmol), 15 (23 mg, 0.053 mmol), $ZnCl_2$ (60 mg, 0.44 mmol) in 2 ml of DMF. Yield: 2.2 mg of (2a) and 1.8 mg of (2b) as $NH_4^+$ salts. A schematic of the synthesis is shown if FIG. 3.

$m^7Gp_sppG$ D1 and D2 (3a, 3b). This compound was synthesized as described for (1) starting from (10) (58 mg, 0.090 mmol), (12) (120 mg, 0.22 mmol), $ZnCl_2$ (249 mg, 1.8 mmol) in 3.5 ml of DMF. Yield: 14.7 mg of (3a) and 10.1 mg of (3b) as $NH_4^+$ salts. A schematic of the synthesis is shown if FIG. 2.

$m_2^{7,2'-O}Gppp_sG$ D1 and D2 (4a, 4b). Compounds (9) (48 mg, 0.084 mmol) and (8) (57 mg, 0.10 mmol) were suspended in 2 ml of DMF. Subsequently, anhydrous $ZnCl_2$ (115 mg, 0.84 mmol) was added. The resulting solution was maintained at RT for 2 days. The reaction was quenched by addition of 350 mg of EDTA in 30 ml of water and neutralized with solid sodium bicarbonate. Products were separated by semi-preparative RP HPLC using linear gradient of methanol in 0.05M ammonium acetate, pH=5.9, from 0-50% within 45 min. Yield: 5.2 mg of (4a) and 7.4 mg of (4b) as $NH_4^+$ salts. A schematic of the synthesis is shown if FIG. 1.

$m_2^{7,2'-O}Gpp_spG$ D1 and D2 (5a, 5b). This compound was synthesized as described for (4) starting from (17) (106 mg, 0.16 mmol), (15) (103 mg, 0.24 mmol) and $ZnCl_2$ (260 mg, 1.9 mmol) in 5 ml of DMF. The reaction was quenched with 800 mg of EDTA in 100 ml of water and neutralized with solid sodium bicarbonate. Products were separated by semi-preparative RP HPLC using isocratic 0.05M ammonium acetate, pH=5.9. Yield: 10.0 mg; of (5a) and 12.1 mg of (5b) as $NH_4^+$ salts. A schematic of the synthesis is shown if FIG. 3.

$m_2^{7,2'-O}Gpp_spG$ D1 and D2 (6a, 6b). This compound was synthesized as described for (4) starting from (11) (70 mg, 0.15 mmol), (12) (107 mg, 0.20 mmol) and anhydrous $ZnCl_2$ (220 mg, 1.6 mmol) in 3 ml of DMF. The reaction was quenched with 650 mg of EDTA in 70 ml of water. Products were separated by semi-preparative RP HPLC using linear gradient of methanol in 0.05M ammonium acetate, pH=5.9, from 0-50% within 45 min. Yield: 15 mg of (6a) and 20 mg of (6b) as $NH_4^+$ salts. A schematic of the synthesis is shown if FIG. 2.

The structures and homogeneity of the above final compounds were confirmed by re-chromatography on RP HPLC, mass spectrometry using negative electro spray ionization (MS ESI-) and $^1H$ NMR and $^{31}P$ NMR spectroscopy. The results are shown below in Table 1.

TABLE 1

$^1H$ NMR chemical shifts in parts per million (±0.01) versus internal sodium 3-trimethylsilyl-[2,2,3,3-$^2H_4$]-propionate and $^{31}P$ NMR chemical shifts in parts per million (±0.01) versus external $H_3PO_4$.

|  | 1a | | 1b | | 2a | | 2b | | 3a | | 3b | |
| --- | --- | --- | --- | --- | --- | --- | --- | --- | --- | --- | --- | --- |
|  | $m^7G$ | G | $m^7G$ | G | $m^7G$ | G | $m^7G$ | G | $m^7G$ | G | $m^7G$ | G |
| H8 | —$^a$ | 8.22 | —$^a$ | 8.14 | 9.00$^b$ | 8.04 | 9.01$^b$ | 7.94 | 9.11$^b$ | 8.01 | 9.08$^b$ | 8.01 |
| H1' | 5.92 | 5.85 | 5.91 | 5.84 | 5.83 | 5.74 | 5.84 | 5.74 | 5.92 | 5.79 | 5.90 | 5.79 |
| H2' | 4.58 | 4.62 | 4.58 | 4.62 | 4.58 | 4.60 | 4.45 | 4.71 | 4.58 | 4.69 | 4.54 | 4.67 |
| H3' | 4.46 | 4.47 | 4.46 | 4.47 | 4.49 | 4.54 | 4.42$^c$ | 4.42$^c$ | 4.50 | 4.49 | 4.49 | 4.42 |
| H4' | 4.35$^c$ | 4.35$^c$ | 4.35$^c$ | 4.35$^c$ | 4.27$^c$ | 4.36$^c$ | 4.36$^c$ | 4.39$^c$ | 4.34$^c$ | 4.39$^c$ | 4.36$^c$ | 4.42$^c$ |
| H5' | 4.38$^c$ | 4.31$^c$ | 4.38$^c$ | 4.31$^c$ | 4.42 | 4.27$^c$ | 4.39$^c$ | 4.22$^c$ | 4.38$^c$ | 4.27 | 4.37$^c$ | 4.29$^c$ |
| H5" | 4.26$^c$ | 4.31$^c$ | 4.26$^c$ | 4.31$^c$ | 4.36$^c$ | 4.27$^c$ | 4.36$^c$ | 4.20$^c$ | 4.33$^c$ | 4.26 | 4.35$^c$ | 4.29$^c$ |
| $CH_3$ (N7) | 4.07 | — | 4.05 | — | 4.06 | — | 4.03 | — | 4.07 | — | 4.07 | — |
| Pα | 44.17 | | 44.17 | | −12.37 | | −12.37 | | −11.26 | | −11.26 | |
| Pβ | −23.86 | | −23.86 | | 30.27 | | 30.18 | | −23.79 | | −23.79 | |
| Pγ | −11.29 | | −11.29 | | −12.37 | | −12.37 | | 43.66 | | 43.26 | |

|  | 4a | | 4b | | 5a | | 5b | | 6a | | 6b | |
| --- | --- | --- | --- | --- | --- | --- | --- | --- | --- | --- | --- | --- |
|  | $m_2^{7,2'-O}G$ | G | $m_2^{7,2'-O}G$ | G | $m_2^{7,2'-O}G$ | G | $m_2^{7,2'-O}G$ | G | $m_2^{7,2'-O}G$ | G | $m_2^{7,2'-O}G$ | G |
| H8 | —$^a$ | 8.10 | —$^a$ | 8.07 | 9.01$^b$ | 8.03 | 9.02$^b$ | 8.01 | 9.08$^b$ | 8.01 | 9.06$^b$ | 8.01 |
| H1' | 5.94 | 5.81 | 5.93 | 5.80 | 5.97 | 5.80 | 5.93 | 5.78 | 5.95 | 5.79 | 5.93 | 5.78 |
| H2' | 4.26 | 4.68 | 4.21 | 4.66 | 4.24 | 4.68 | 4.25$^c$ | 4.68 | 4.23 | 4.68 | 4.18 | 4.66 |
| H3' | 4.56 | 4.50 | 4.52 | 4.48$^c$ | 4.54 | 4.49 | 4.54 | 4.49 | 4.56 | 4.50 | 4.49$^c$ | 4.49$^c$ |
| H4' | 4.30$^c$ | 4.37$^c$ | 4.33$^c$ | 4.35$^c$ | 4.33$^c$ | 4.27$^c$ | 4.31$^c$ | 4.26$^c$ | 4.33 | 4.28 | 4.30$^c$ | 4.30$^c$ |
| H5' | 4.39$^c$ | 4.30$^c$ | 4.46$^c$ | 4.28$^c$ | 4.41 | 4.30$^c$ | 4.41 | 4.30$^c$ | 4.40 | 4.33$^c$ | 4.30$^c$ | 4.30$^c$ |

| | | | | | | | | | | | |
|---|---|---|---|---|---|---|---|---|---|---|---|
| H5" | 4.30$^c$ | 4.30$^c$ | 4.34$^c$ | 4.26$^c$ | 4.32$^c$ | 4.27$^c$ | 4.34$^c$ | 4.27$^c$ | 4.33$^c$ | 4.28 | 4.30$^c$ | 4.30$^c$ |
| CH$_3$ (N7) | 4.08 | — | 4.07 | — | 4.06 | — | 4.07 | — | 4.08 | — | 4.08 | — |
| CH$_3$ (2'-O) | 3.59 | — | 3.59 | — | 3.60 | — | 3.58 | — | 3.59 | — | 3.59 | — |
| Pα | 43.61 | | 43.70 | | −12.10 | | −12.10 | | −11.25 | | −11.32 | |
| Pβ | −23.86 | | −23.80 | | 30.33 | | 30.23 | | −23.85 | | −23.72 | |
| Pγ | −11.33 | | −11.34 | | −12.10 | | −12.10 | | 43.63 | | 43.13 | |

$^a$-exchangeable protons;
$^b$-exchangeable but visible protons;
$^c$-approximate value because of signal overlapping

EXAMPLE 6

Synthesis of Tetraphosphate S-ARCA

Figure 4:
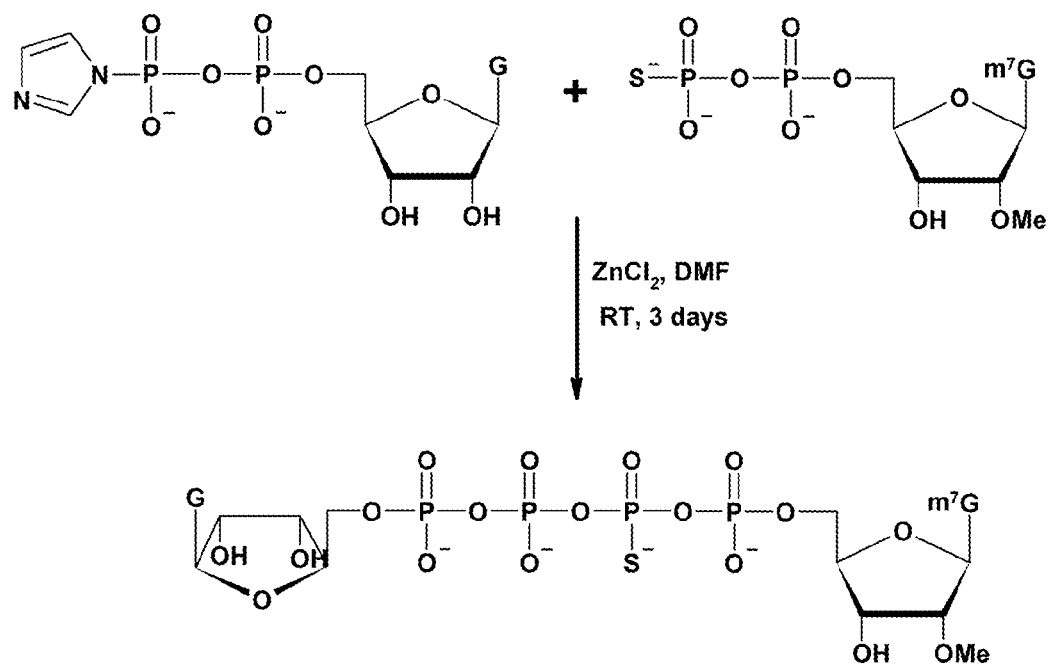
FIG. 4 depicts the synthesis for a tetraphosphate γ S-ARCA, $m_2^{7,2'-O}Gpp_sppG$ (D1 and D2).

The utility of the developed strategy for the synthesis of S-ARCAs containing 5',5'-tetraphosphate bridge was shown by the synthesis of m$_2^{7,2'\text{-}O}$Gpp$_s$ppG (FIG. 4). The synthesis of three other tetraphosphate S-ARCAs (i.e. m$_2^{7,2'\text{-}O}$Gp$_s$pppG, m$_2^{7,2'\text{-}O}$Gppp$_s$pG, m$_2^{7,2'\text{-}O}$Gpppp$_s$G) is available via analogous approach.

m$_2^{7,2'\text{-}O}$Gpp$_s$ppG (D1 and D2).

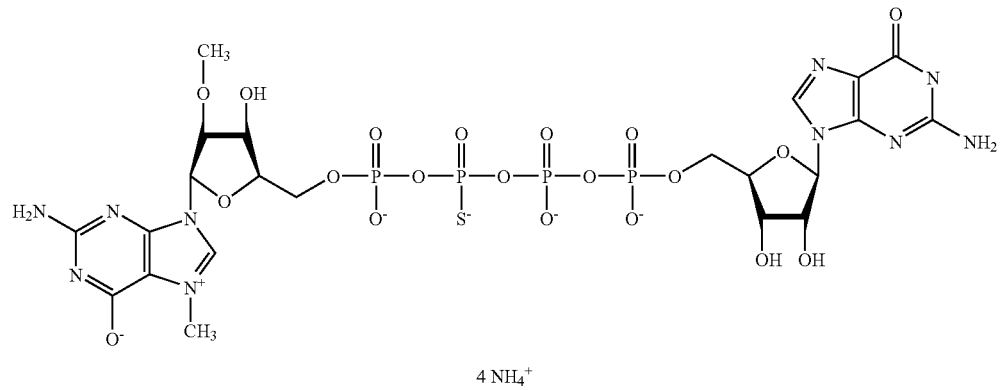

4 NH$_4^+$ 7,2'-O-dimethylguanosine 5'-(thiodiphosphate) (20 mg, 0.029 mmol) and guanosine 5'-diphosphate imidazolide (30 mg, 0.056 mmol) were suspended in 2 ml of DMF. Subsequently, anhydrous ZnCl$_2$ (61 mg, 0.45 mmol) was added. The resulting solution was stirred at room temperature for 3 days. The reaction was quenched by addition of EDTA (166 mg, 0.45 mmol) in 20 ml of water, and neutralized with solid sodium bicarbonate. Products were separated by ion exchange DEAE Sephadex chromatography using a 0-1.2 M gradient of TEAB. Fractions containing a diastereomeric mixture of m$_2^{7,2'\text{-}O}$Gpp$_s$ppG were collected, poured together and evaporated under reduced pressure with repeated addition of ethanol. Final purification was achieved by semi-preparative RP HPLC, using a linear gradient of methanol in 0.05M ammonium acetate, pH=5.9, from 0-25% within 60 min. Yield: 7 mg of m$_2^{7,2'\text{-}O}$Gpp$_s$ppG (diastereomeric mixture) as NH$_4^+$ salt.

MS ESI (−): Calc. for C$_{22}$H$_{30}$N$_{10}$O$_{17}$P$_3$S, 897.02. found: 879.09

D1: $^1$H NMR: δ (ppm) 9.14 (1H, s) 8.08 (1H, s), 5.99 (1H, d), 5.813 (1H, d); 4.70 (1H; t), 4.64 (1H, t), 4.54 (1H, t), 4.45 (1H, m), 4.35 (2H, m), 4.29 (3H, m), 4.07 (3H, s), 3.60 (3H, s); $^{31}$P NMR: δ 30.2 (1P, t, Pγ), −11.1 (1P, dd, Pδ), −11.9 (1P, dd, Pα), −23.8 (1P, d, Pβ)

D2: $^1$H NMR: δ (ppm) 9.16 (1H, s) 8.08 (1H, s), 6.03 (1H, d), 5.83 (1H, d); 4.70 (1H; t), 4.60 (1H, t), 4.54 (1H, t), 4.45 (1H, m), 4.35 (2H, m), 4.29 (3H, m), 4.07 (3H, s), 3.58 (3H, s); $^{31}$P NMR: δ 30.2 (1P, t, Pγ), −11.1 (1P, dd, Pδ), −11.9 (1P, dd, Pα), −23.8 (1P, d, Pβ)

EXAMPLE 7

Synthesis of S-ARCA with Two Phosphorothioate Moieties

Figure 5:
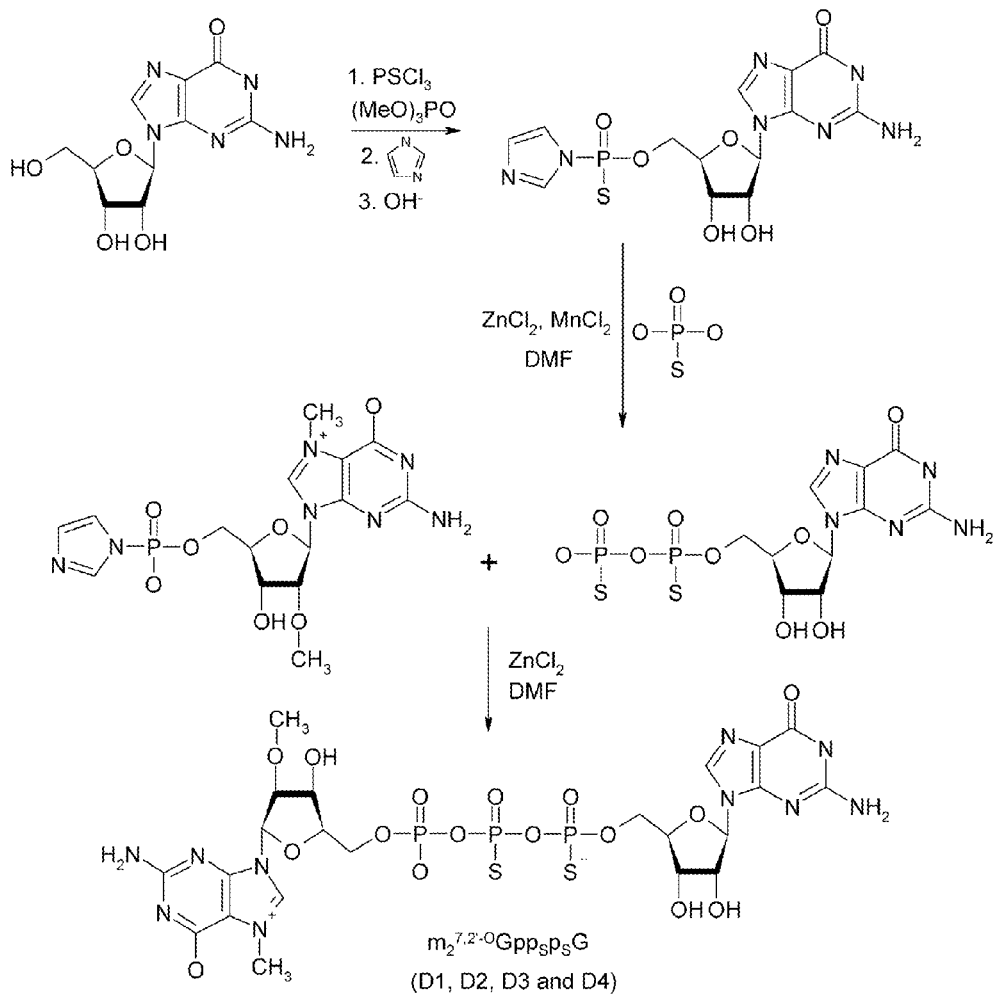
FIG. 5 depicts the synthesis for a S-ARCA with two phosphorothioate moieties the α and β positions in a triphosphate bridge, $m_2^{7,2'-O}Gpp_sp_sG$ (D1, D2, D3 and D4).

The developed strategy offers also a way to synthesize compounds containing multiple phosphorothioate moieties in the 5',5'-polyphosphate bridge that may be achieved by the synthetic route suggested in FIG. 5, for example, compound m$_2^{7,2'\text{-}O}$Gpp$_s$p$_s$G. Imidazolide derivative of guanosine 5'-O-thiophosphate will be prepared analogously to the procedure reported previously for imidazolide derivative of adenosine 5'-O-thiophosphate [M. Shimazu et al. "Regio- and stereo-controlled synthesis of 2'-5'-linked phosphorothioate oligoadenylates by uranyl ion catalyst in aqueous solution", J. Chem. Soc., Perkin Trans. 1, 2002, 1778-1785] and purified on DEAE Sephadex A-25 column with a linear gradient of triethylammonium bicarbonate (from 0 to 0.5 M TEAB in deionized water). A depiction of the synthesis is shown in FIG. 5.

Guanosine 5'-O-(1,2-dithiodiphosphate). Imidazolide derivative of guanosine 5'-O-monothiophosphate (triethylammonium salt, 53 mg, 0.1 mmol) will be mixed with phosphorothioate triethylammonium salt (320 mg, ca 1.2 mmol) and the resultant mixture suspended in 3.5 mL of DMF. Subsequently, anhydrous zinc chloride (55 mg, 0.4 mmol) and manganese chloride (50 mg, 0.4 mmol) will be added. The reaction will be quenched by addition of EDTA solution (270 mg, 0.8 mmol in 35 mL of water) and brought to pH 7 with sodium bicarbonate. Chromatographic isolation will be performed on a DEAE-Sephadex A-25 column with a linear gradient of triethylammonium bicarbonate (from 0 to 0.9 M TEAB in deionized water). Fractions containing guanosine 5'-O-(1,2-dithiodiphosphate) will be collected and evaporated under reduced pressure with addition of ethanol and the resultant solid was dried in vacuo over $P_4O_{10}$.

$m_2^{7,2'-O}Gpp_sp_sG$. Imidazolide derivative of 7,2'-O-dimethylguanosine 5'-O-monophosphate (sodium salt, 23 mg, 0.05 mmol) will be mixed with guanosine 5'-O-(1,2-dithiodiphosphate) (triethylammonium salt, 39 mg, 0.05 mmol) and the resultant mixture suspended in 1.5 mL of DMF. Subsequently, anhydrous zinc chloride (55 mg, 0.4 mmol) will be added. The reaction will be quenched by addition of EDTA solution (135 mg, 0.4 mmol in 20 mL of water) and brought to pH 7 with sodium bicarbonate. Chromatographic isolation and separation of $m_2^{7,2'-O}Gpp_sp_sG$ diastereomers (D1, D2, D3, D4) will be performed by semi-preparative RP HPLC.

EXAMPLE 8

Cell Culture

HC11 mammary epithelial cells are clonally derived from the COMMA-1D mouse mammary gland cells line. See K. Danielson et al. "Epithelial mouse mammary cell line exhibiting normal morphogenesis in vivo and functional differentiation in vitro," *Proc. Natl. Acad. Sci. U.S.A.*, vol. 81, pp. 3756-3760 (1984). The cells were grown in RPMI 1640 medium containing 10% bovine growth serum (HyClone), 5 µg/ml bovine insulin (Sigma), and 10 ng/ml recombinant EGF (BD Biosciences).

EXAMPLE 9

In Vitro Synthesis of mRNAs

Capped RNAs were synthesized by in vitro transcription in the presence a luciferase-encoding plasmid (pluc-$A_{60}$), with T7 polymerase, in the presence of all four nucleoside triphosphates and different cap dinucleotides. See J. Jemielity et al. "Novel 'anti-reverse' cap analogues with superior translational properties," *RNA*, vol. 9, pp. 1108-1122 (2003). A typical transcription reaction contained 40 mM Tris-HCl, pH 7.9, 6 mM $MgCl_2$, 2 mM spermidine, 10 mM DTT, 0.1 mg/ml BSA, 1 U/µl of RNasin (Promega), 0.5 mM ATP, 0.5 mM CTP, 0.5 mM UTP, 0.1 mM GTP, 1 mM cap analog, 15 µg/ml DNA, and 1 U/µl of T7 polymerase (Promega). pluc-$A_{60}$, which contains the entire firefly luciferase coding sequence in pGEM4 (Promega) and a 3'-terminal 60-nt poly(A) tract (see E. Grudzien et al., "Differential inhibition of mRNA degradation pathways by novel cap analogs," *J. Biol. Chem.*, vol. 281, pp. 1857-1867 (2006)), was digested with HpaI for synthesis of luciferase mRNA, and with NcoI for synthesis of capped oligonucleotides.

Short RNAs (capped oligonucleotides of about 48 nt) were synthesized in the presence of 10 µCi/µl of [α-$^{32}$P]GTP (ICN) in 50-µl reaction mixtures incubated for 45 min at 37° C. Reaction mixtures were extracted with phenol and chloroform, and then RNAs were separated from unincorporated nucleotides using spin columns (Ambion), according to the manufacturer's protocol. The concentrations of mRNAs were determined by Cerenkov counting in which the specific radioactivity of [α-$^{32}$P]GTP in the final transcription reaction mixture was used for conversion of cpm to pmol.

mRNAs were synthesized in 200-µl reaction mixtures incubated for 45 min at 37° C. After incubation, 200-µl reaction mixtures were treated with 3 units of DNase RQ1 (Promega) for 20 min at 37° C., and RNA was purified with an RNeasy mini kit (Qiagen) using the manufacturer's protocol. The concentrations of RNAs were determined spectrophotometrically.

EXAMPLE 10

In Vitro RNA Decapping Assay

Dcp2 activity was measured with capped 48-nt oligonucleotides as substrates, a truncated form of luciferase mRNA (48 nucleotides). GST-hDcp2 was expressed in *Escherichia coli* and purified as described by Z. Wang et al., "The hDcp2 protein is a mammalian mRNA decapping enzyme," *Proc. Natl. Acad. Sci. U.S.A.*, vol. 99, pp. 12663-12668 (2002). Capped oligonucleotides were first subjected to digestion with GST-hDcp2 at 37° C. for 2 h in decapping buffer (10 mM Tris-HCl, pH 7.5, 100 mM potassium acetate, 2 mM magnesium acetate, 0.5 mM $MnCl_2$, 2 mM dithiothreitol, and 0.1 mM spermine). See C. Piccirillo et al., "Functional characterization of the mammalian mRNA decapping enzyme hDcp2," *RNA*, vol. 9, pp. 1138-1147 (2003). The reaction mixture was then extracted once with an equal volume of phenol and twice with chloroform, and RNA was precipitated with ethanol. Products of the decapping reaction were further digested with a cocktail of ribonucleases (RiboShredder; Epicentre) at 37° C. for 1 h. The products were resolved by anion-exchange HPLC on a 4.6×250-mm Partisil 10SAX/25 column (Whatman). The gradient consisted of water for 1 min, a linear gradient to 112 mM $KH_2PO_4$, pH 4.5, for 20 min, a linear gradient of 112-450 mM $KH_2PO_4$ for 15 min, a linear gradient of 450 mM to 1.5 M $KH_2PO_4$ for 15 min, and isocratic elution at 1.5 M of $KH_2PO_4$ for 9 min, all at a flow rate 1 ml/min.

EXAMPLE 11

Measurement of Translational Efficiency and mRNA Decay in HC11 Cells

Two methods, electroporation and nucleoporation, were used to deliver RNA into cells. In case of electroporation, 5 µg of RNA were introduced into $10^7$ HC11 cells in a total volume 400 µl of serum-reduced RPMI 1640 medium in a Gene pulser cuvette (4 mm gap) with a Bio-Rad Genepulser™ set at 0.22 kV and 960 µF. Following discharge, the cells were washed twice with PBS, centrifuged for 2 min 300×g at room temperature, resuspended in prewarmed complete medium, and placed at 37° C. Nucleoporation was performed with an Amaxa Nucleofector II (Amaxa Biosystems) in accordance with manufacture's recommendations. One microgram of RNA was introduced into $10^6$ HC11 cells with Nucleofector Solution V and the set of recommended regimens (program T-024).

For measurement of translational efficiency, cells were divided into several Eppendorf tubes, placed in a water bath at 37° C., and shaken. For measurement of mRNA stability, cells were distributed into 35-mm cell culture dishes and placed at 37° C. in a 5% $CO_2$ humidified atmosphere. Cells were harvested at various times and washed twice with PBS.

For cytoplasmic RNA extraction, $2×10^5$ cells were lysed in 175 µl of lysis buffer (50 mM Tris-HCl, pH 8.0, 140 mM NaCl, 1.5 mM $MgCl_2$, 0.5% (v/v) Igepal (Sigma), and 1 mM dithiothreitol). RNAs were further purified using the RNeasy mini kit. For protein extraction, $2×10^5$ cells were lysed in 200 µl of Luciferase Cell Culture Lysis Reagent (Promega). Luciferase activity of cell extracts was measured according to the manufacturer's protocol (Promega).

EXAMPLE 12

Preparation of Polysomes

To separate ribosomal subunits and initiation complexes, $4×10^6$ HC11 cells were treated for 2 min with ice-cold PBS containing 0.1 mg/ml cycloheximide, washed twice with the same medium, and lysed in 600 µl of 0.3 M NaCl, 15 mM Tris-HCl (pH 7.6), 15 mM $MgCl_2$, 1% Triton X-100, 1 mg/ml heparin, and 0.1 mg/ml cycloheximide. After centrifugation at 14,000×g for 10 min, the supernatant was layered on a 15-45% sucrose gradient in the same buffer but lacking Triton X-100 and centrifuged in a Beckman SW41 Ti rotor at 38,000 rpm at 4° C. for 2 h. Gradients were fractionated with continuous monitoring of absorbance at 260 nm. RNA from each fraction (1 ml) was isolated and analyzed by real time PCR.

EXAMPLE 13

Real Time PCR

For measurement of mRNA stability, approximately 2 μg of each total RNA sample isolated from HC11 cells and purified with an RNeasy mini kit (Qiagen) were treated with 3 units of DNase RQ1 (Promega) for 20 min at 37° C. Reverse transcription was performed on 400 ng of RNA in 20-μl reaction mixtures containing 5.5 mM $MgCl_2$, 500 μM of each dNTP, 2.5 μM random hexamers, 0.2 units of RNase inhibitor, and 0.8 units of MultiScribe reverse transcriptase (Applied Biosystems). Reaction mixtures were incubated at 25° C. for 10 min, 48° C. for 30 min, and 95° C. for 5 min. Quantitative real time PCR was performed with specific primers designed for each mRNA with the Beacon Designer tool (Bio-Rad). For detecting sequences at the 5'-end of luciferase mRNA, the primers were 5'-CGTTCGGTTGGCAGAAGCTA-3' (SEQ ID NO: 1) and 5'-ACTGTTGAGCAATTCACGTTCATT-3' (SEQ ID NO: 2). Luciferase mRNA from the cap structure to the beginning of the 3'-terminal homopolymer tract consisted of 1714 nucleotides. These primers amplified nucleotides 226-398. Mouse GAPDH mRNA levels were measured by the same method and in the same RNA samples with the primers 5'-CAATGTGTCCGTCGTGGATCT-3' (SEQ ID NO: 3) and 5'-GAAGAGTGGGAGTTGCTGTTGA-3' (SEQ ID NO: 4).

Amplification and detection were performed with the iCycler IQ real time PCR detection system in 25-μl reaction mixtures containing 5 μl of the transcription reaction mixture (50 ng of cDNA), 12.5 μl of IQ SYBRgreen Supermix, and 0.3 mM primers (Bio-Rad). The incubation conditions were 3 min at 95° C. for polymerase activation, and 40 cycles of 15 s at 95° C. and 1 min at 60° C.

Luciferase mRNA levels were calculated using the absolute standard curve method as described in User Bulletin No. 2 for the ABI Prism 7700 Sequence Detection System. After the amount of luciferase mRNA was calculated from a standard curve, it was normalized for the amount of mouse GAPDH mRNA in each sample. The amount of luciferase mRNA remaining at each time point was converted to a percent of the RNA present at zero time, and the results were plotted as $\log_{10}$([RNA]) versus time to determine half-life. For analysis of RNA from polysome gradients, in vitro-synthesized GFP mRNA was added to each fraction before RNA isolation as an internal standard to control variation in RNA yield. The level of GFP mRNA was used to normalize the levels of luciferase and GAPDH mRNA.

EXAMPLE 14

Binding Affinities for eIF4E

Binding affinities of S analogs for murine eIF4E were determined by fluorescence quenching. Fluorescence titration measurements were carried out on an LS-50B spectrofluorometer (Perkin Elmer Co.) in 50 mM HEPES/KOH (pH 7.2), 100 mM KCl, 0.5 mM EDTA, 1 mM DTT at 20.0±0.2° C. Aliquots of 1 μl increasing concentration of cap analogue solutions were added to 1.4 ml of 0.1 protein solutions. Fluorescence intensities (excitation at 280 nm with 2.5 nm bandwidth and detection at 337 nm with 4 nm bandwidth and 290 nm cut-off filter) were corrected taking into account sample dilution and the inner filter effect. Equilibrium association constants ($K_{AS}$) were determined by fitting the theoretical dependence of the fluorescence intensity on the total concentration of cap analogue to the experimental data points according to equation described previously (See A. Niedzwiecka et al., "Biophysical studies of eIF4E cap-binding protein: recognition of mRNA 5' cap structure and synthetic fragments of eIF4G and 4E-BP1 proteins," J. Mol. Biol., vol. 319, pp. 615-635 (2002)). The concentration of protein was fitted as a free parameter of equilibrium equation showing amount of "active" protein. The final $K_{AS}$ was calculated as a weighted average of three to ten independent titrations, with the weights taken as the reciprocals of the numerical standard deviations squared. Numerical nonlinear least-squares regression analysis was performed using ORGIN 6.0 (Microcal Software Inc., USA). The Gibbs free energy of binding was calculated from the $K_{AS}$ value according to the standard equation $\Delta G° = -RT \ln K_{AS}$.

EXAMPLE 15

Enzymatic Hydrolysis by Human and *C. elegans* DcpS

Human and nematode DcpS were expressed in *Escherichia coli* according to the procedures described previously (L. S. Cohen et al., "Nematode m7 GpppG and m3(2,2,7)GpppG decapping: activities in *Ascaris* embryos and characterization of *C. elegans* scavenger DcpS," RNA, vol. 10, pp. 1609-1624 (2004)). Both proteins were stored at −80° C. in 20 mM Tris buffer, pH 7.5, containing 50 mM KCl, 0.2 mM EDTA, 1 mM DTT, 0.5 mM PMSF, and 20% glycerol. An appropriate cap analog at 1 mM concentration was treated with 5.0 or 7.0 μl of DcpS (from human or *C. elegans*, respectively) in 500 μl of 50 mM TRIS buffer, pH=7.9, containing 20 mM of $MgCl_2$ and 60 mM of $(NH_4)_2SO_4$ at 37° C. for 60-90 min. Every 15-20 min a 100 μl sample was collected from the reaction mixture and deactivated by incubation in 90° C. for 3 min. Collected samples were analyzed without further treatment by analytical RP HPLC using a linear gradient of methanol in 0.1 M $KH_2PO_4$, pH=6.0, from 0-50% within 15 min and UV-detection at 260 nm.

EXAMPLE 16

Inhibition of Cap-Dependent Translation

A micrococcal nuclease-treated rabbit reticulocyte lysate was used for in vitro translation (A. Cai et al., "Quantitative assessment of mRNA cap analogues as inhibitors of in vitro translation," Biochemistry, vol. 38, pp. 8538-8547 (1999)). Optimal cap-dependent translation was achieved at 100 mM potassium acetate and 1.4 mM magnesium chloride. To determine inhibition of translation by various cap analogs, natural rabbit globin mRNA was added to the lysate at the concentration 5 μg/ml, and protein synthesis was measured by incorporation of [$^3$H]Leu. Normalization of $K_I$ data was performed as described previously (Cai et al., 1999). The concentrations of dinucleotide cap analog solutions were measured by UV absorption at pH 7.0 using $\lambda=255$ nm and $\epsilon_m=22.6\times10^{-3}$ M.

Results

EXAMPLE 17

Synthesis of Cap Analogs

The synthetic pathways leading to analogs possessing the phosphorothioate group in the α, γ, and β positions of the triphosphate chain are depicted in FIGS. 1, 2, and 3, respectively.

We synthesized a series of six cap analogs bearing a single phosphorothioate moiety at either the α, β, or γ positions of the 5',5'-triphosphate chain. (See below.) Due to the presence of stereogenic P-center, each S-analog was obtained as a mixture of two diastereomers, designated D1 and D2 according to their elution order during RP HPLC. Each S-analog was successfully resolved by RP HPLC, providing twelve compounds that were subsequently characterized biophysically and biochemically. Six of the S-analogs contained an ARCA modification, a 2'-O-methyl group in the m7Guo moiety, and are hence are termed S-ARCAs. Introduction of a phosphorothioate group at the β position produced resistance to Dcp2, increased half-life and improved translational efficiency.

See J. Kowalska et al., "A simple and rapid synthesis of nucleotide analogues containing a phosphorothioate moiety at the terminal position of the phosphate chain", *Tetrahedron Lett* Vol. 48, 2007, 5475-5479. The reaction strategy we have developed enables introduction of the phosphorothioate moiety at selected positions of the polyphosphate chain, as well as production of intermediate nucleosides 5'-(2-thiodiphosphates).

As shown above and as used in the claims, the phosphate moiety that is named "α" is the phosphate moiety most distal to the 7-methylguanosine moiety. The position named "β" is

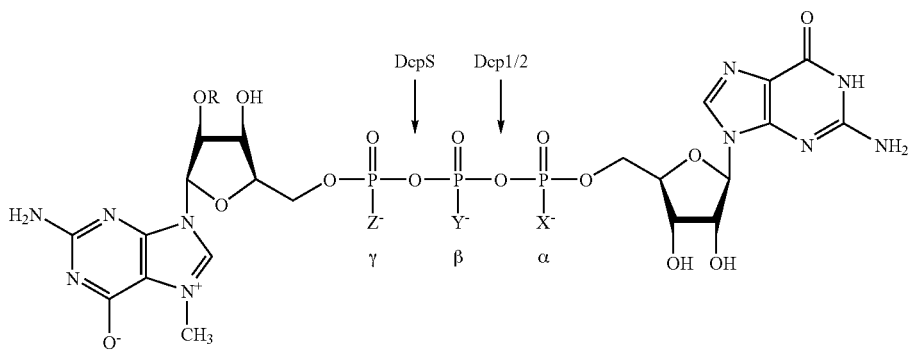

| Compound | Abbreviation | X | Y | Z | R | Configuration |
|---|---|---|---|---|---|---|
| 1a | m7Gppp$_s$G (D1) | S | O | O | H | S$_p$ |
| 1b | m7Gppp$_s$G (D2) | S | O | O | H | R$_p$ |
| 2a | m7Gpp$_s$pG (D1) | O | S | O | H | n.a. |
| 2b | m7Gpp$_s$pG (D2) | O | S | O | H | n.a. |
| 3a | m7Gp$_s$ppG (D1) | O | O | S | H | n.a. |
| 3b | m7Gp$_s$ppG (D2) | O | O | S | H | n.a. |
| 4a | m2$^{7,2'-O}$Gppp$_s$G (D1) | S | O | O | CH$_3$ | S$_p$ |
| 4b | m2$^{7,2'-O}$Gppp$_s$G (D2) | S | O | O | CH$_3$ | R$_p$ |
| 5a | m2$^{7,2'-O}$Gpp$_s$pG (D1) | O | S | O | CH$_3$ | n.a. |
| 5b | m2$^{7,2'-O}$Gpp$_s$pG (D2) | O | S | O | CH$_3$ | n.a. |
| 6a | m2$^{7,2'-O}$Gp$_s$ppG (D1) | O | O | S | CH$_3$ | n.a. |
| 6b | m2$^{7,2'-O}$Gp$_s$ppG (D2) | O | O | S | CH$_3$ | n.a. | n.a.-not assigned

The chemical synthesis of S-ARCAs was a modification of that originally developed for cap analogs with unmodified 5',5'-polyphosphate bridges. See M. Kadokura et al., "Efficient synthesis of γ-methyl-capped guanosine 5'-triphosphate as a 5'-terminal unique structure of U6 RNA via a new triphosphate bond formation involving activation of methyl phosphorimidazolidate using ZnCl$_2$ as a catalyst in DMF under anhydrous conditions," *Tetrahedron Lett.*, vol. 38, pp. 8359-8362 (1997); J. Stepinski et al., "Synthesis and properties of mRNAs containing the novel "anti-reverse" cap analogues 7-methyl(3'-O-methyl)GpppG and 7-methyl(3'-deoxy)GpppG," *RNA*, vol. 7, pp. 1486-1495 (2001), and J. Jemielity et al., "Novel 'anti-reverse' cap analogues with superior translational properties," *RNA*, vol. 9, pp. 1108-1122 (2003). Two mononucleotide species, one of which is first converted into a reactive imidazolide derivative, are coupled in DMF. The reaction is facilitated by an 8-fold excess of ZnCl$_2$, which significantly improves the solubility of the reactants in organic media, prevents the hydrolysis of imidazolide derivatives, and accelerates the reaction rate. An important step in the synthesis was coupling of an appropriate imidazolide derivative with a nucleoside 5'-phosphorothioate or 5'-(2-thiodiphosphate) in DMF in the presence of ZnCl$_2$. The intermediate nucleoside 5'-(2-thiodiphosphates) were efficiently obtained in a similar, recently developed reaction, that employs the thiophosphate anion (PSO$_3^{3-}$) as nucleophile.

the next phosphate in the direction moving toward the 7-methylguanosine moiety, and the position named "γ" is the next phosphate in the direction moving toward the 7-methylguanosine moiety. In the triphosphate ARCAs, as shown above, the "γ" is the phosphate closest to the 7-methylguanosine moiety. In the tetraphosphate ARCAs, the "γ" is separated from the 7-methylguanosine moiety by the "δ" phosphate. (In ARCAs without a 7-methylguanosine moiety, it will be understood that the preceding definition should be modified to refer to instead to the moiety with the position that is analogous to that of the 7-methylguanosine in the examples given here.)

The synthetic pathway leading to analogs 1 and 4 modified at the α-position of the 5',5'-triphosphate bridge (i.e., m7Gppp$_s$G and m2$^{7,2'-O}$Gppp$_s$G) is depicted in FIG. 1. In both final coupling reactions, a 1.5- to 2-fold excess of phosphorimidazolide was used to ensure complete consumption of the nucleoside 5'-thiophosphate. The coupling proceeded steadily, leading to almost complete consumption of the substrate within 1-2 days. The synthesis of analogs 3 and 6 modified at the γ position (i.e., m7Gp$_s$ppG and m2$^{7,2'-O}$Gp$_s$ppG), which is depicted in FIG. 2, was similar to the one described above. In each case, formation of two diastereomers was indicated by RP HPLC as shown in FIG. 2. The intermediate nucleoside 5'-thiophosphates 9, 10 and 11 were synthesized via thiophosphorylation of appropriate nucleosides by PSCl$_3$ in trimethyl phosphate in the presence of 2,6-dimethylpirydine at 0° C., similar to the previously reported procedures (J. R. Moran et al., "A practical enzymatic synthesis of (S [P])-adenosine 5'-O-(1-thiotriphosphate) ((S[P])-ATP-á-S)," J. Org. Chem., vol. 49, pp. 704-706 (1984)). In the case of compounds 10 and 11, the methylation at N7 position had to be performed at the stage of the nucleoside, before the thiophosphorylation step, because otherwise methyl iodide preferably alkylates the sulfur atom (unpublished findings). Conversion of nucleoside 5'-diphosphates into their imidazolide derivatives (7, 8 and 12-15) was easily achieved via reaction with imidazole employing the 2,2'-dithiodipirydine/triphenylphosphine activation system (T. Mukaiyama et al., "Phosphorylation by oxidation-reduction condensation. Preparation of active phosphorylating reagents," Bull. Chem. Soc. Jpn., vol. 44, p. 2284 (1971). The analogs modified at the β-position, i.e., m$^7$Gpp$_s$pG (2) and m$_2^{7,2'-O}$Gpp$_s$pG (5) were synthesized as depicted in FIG. 3. HPLC analysis of the final coupling revealed formation of two P-diastereoisomers. However, their retention times were very similar. To obtain the intermediate nucleoside 5'-O-(2-thiodiphosphates) 16 and 17, we employed a recently developed coupling reaction between a nucleoside 5'-monophosphate imidazolide and thiophosphate (PSO$_3^{3-}$) triethylammonium salt as a nucleophile (J. Kowalska et al., "A simple and rapid synthesis of nucleotide analogues containing a phosphorothioate moiety at the terminal position of the phosphate chain", Tetrahedron Lett Vol. 48, 2007, 5475-5479).

In all reactions leading to cap analogs 1-6, HLPC analysis revealed that the desired compounds were formed as the major products, with only moderate amounts of by-products. Nonetheless, preparative yields were surprisingly lower than those indicated by HPLC, being in the range of 10-20% overall. This is probably due to large losses of material during lengthy separation of diastereoisomers by RP HPLC, which in many cases was performed repeatedly in order to obtain diastereomerically pure samples.

EXAMPLE 18

Decapping Reaction In Vitro

Figure 6:
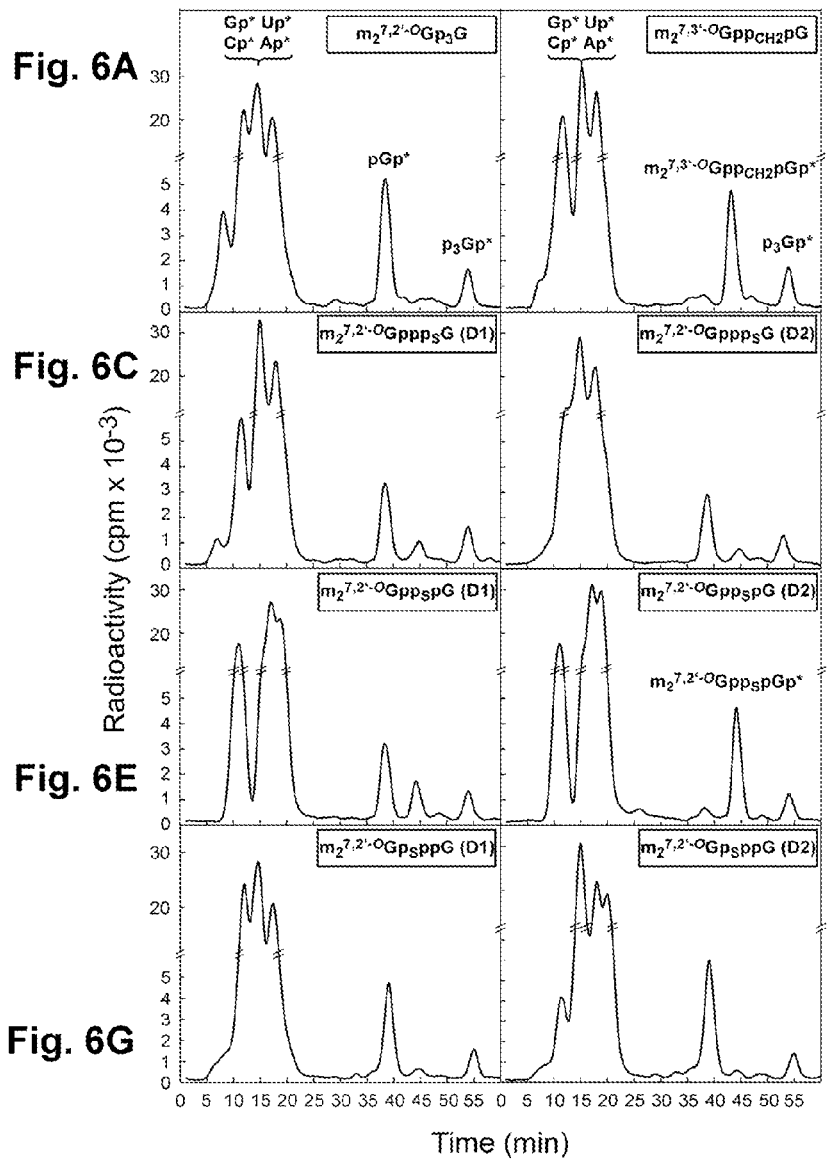
FIGS. 6A-6H depict an analysis of in vitro-synthesized oligonucleotides digested with hDcp2 by anion exchange HPLC.

We tested oligonucleotides capped with either of S-ARCAs for hydrolysis by recombinant hDcp2 to test whether mRNA capped with the various diastereomers of m$_2^{7,2'-O}$Gppp$_s$G and m$_2^{7,2'-O}$Gpp$_s$pG would differ in their sensitivity to cleavage by Dcp1/Dcp2. See generally Z. Wang et al., "The hDcp2 protein is a mammalian mRNA decapping enzyme," Proc. Natl. Acad. Sci. U.S.A., vol. 99, pp. 12663-12668 (2002), and Z. Wang et al., "An mRNA Stability Complex Functions with Poly(A)-Binding Protein To Stabilize mRNA In Vitro", Mol. Cell. Biol., vol. 19, pp. 4552-4560 (1999). Cap analogs used were initially unlabeled, so to follow the products of the digestion reaction we synthesized capped oligonucleotides in the presence of [α-$^{32}$P]GTP and a DNA template in which G was the first ribonucleotide specified after the promoter. The oligonucleotides capped with either of the S-ARCAs were subjected to Dcp2 digestion in vitro, after which the products were further digested with a cocktail of ribonucleases (RiboShredder from Epicenter). Any nucleotide on the 5' side of a G residue acquired a $^{32}$P-labeled 3'-phosphate group after ribonuclease digestion by nearest-neighbor transfer. Anion exchange chromatography was then used to resolve the labeled 3'-nucleoside monophosphates (3'-NMP*), at internal positions in the RNA, from labeled 5'-terminal products (FIG. 6). The latter comprise p$_3$ Gp* derived from uncapped transcripts and m$_2^{7,2'-O}$Gp$_3$ Gp* (when m$_2^{7,2'-O}$Gp$_3$G was used), or pGp* resulting from capped RNA resistant or nonresistant to enzymatic cleavage, respectively. All cap analogs used were ARCAs, which ensured that they were incorporated into RNA exclusively in the correct orientation. This further guaranteed that only one 5'-terminal product (m$_2^{7,2'-O}$Gp$_3$ Gp*) was observed upon ribonuclease treatment. Uncapped RNA is not a substrate for Dcp2, which explains why p$_3$ Gp* product was observed after Dcp2 digestion.

To determine which cap analogs protect mRNA against hDcp2 cleavage, we digested capped-$^{32}$P-labeled short RNA with recombinant hDcp2 employing conditions under which (i) the oligonucleotide capped with m$_2^{7,2'-O}$Gp$_3$G was completely digested by hDcp2 (FIG. 6A) and (ii) the oligonucleotide capped with m$_2^{7,3'-O}$Gpp$_{CH2}$pG was resistant (FIG. 6B). m$_2^{7,3'-O}$G was shown previously to protect mRNA against hDcp2 degradation. See E. Grudzien et al., "Differential inhibition of mRNA degradation pathways by novel cap analogs," J. Biol. Chem., vol. 281, pp. 1857-1867 (2006). We found that only the D2 isomer of m$_2^{7,2'-O}$Gpp$_s$pG stabilized RNA against hDcp2 hydrolysis (FIG. 6F). Oligonucleotides capped with the isomers of m$_2^{7,2'-O}$Gppp$_s$G and m$_2^{7,2'-O}$Gp$_s$ppG showed no increase in stability toward hDcp2 (FIGS. 6C, 6D, 6G, and 6H).

EXAMPLE 19

5' Degradation of mRNAs Capped with Phosphorothioate Cap Analogs

Because short RNAs capped with m$_2^{7,2'-O}$Gpp$_s$pG (D2) were resistant to hDcp2 hydrolysis, we predicted that the presence of this cap analog would affect mRNA stability in cells. We used either nucleoporation or electroporation to introduce synthetic luciferase mRNA into HC11 mouse mammary epithelial cells. These methods allow one to measure luciferase synthesis and luciferase mRNA levels in the cells almost immediately following discharge. For electroporation we used conditions optimized previously. See E. Grudzien et al., "Differential inhibition of mRNA degradation pathways by novel cap analogs," J. Biol. Chem., vol. 281, pp. 1857-1867 (2006). For nucleoportaion we followed conditions recommended by Amaxa Biosystems (see Materials and Methods). Since the Amaxa protocol gave the highest efficiency of transfection and also the highest cell viability, it was used in most experiments described here.

Luciferase mRNAs containing various 5'-terminal caps and a 3'-terminal 60-nt poly(A) tract (Luc-A$_{60}$) were synthesized in vitro. Following nucleoporation, cells were either removed at intervals up to 90 min for measuring translational efficiency, using the rate of luciferase activity increase; or up to 8 h for measuring luciferase mRNA stability by real-time PCR. Determination of translational efficiency and mRNA stability could be erroneous if mRNAs recovered from the cells contained both translated and untranslated mRNA. To address this issue, we determined the rates of degradation for total cytoplasmic mRNA versus polysomal mRNA. Luciferase mRNA capped with m$_2^{7,2'-O}$Gp$_3$G was nucleoporated into HC11 cells, which were then lysed at various times and layered on a sucrose gradient to separate polysomes from initiation complexes. Polysomal fractions were combined, and the RNA purified. To follow cytoplasmic mRNA degradation we used mRNA isolated from total cell extracts. Luciferase mRNA was quantified in both cases by real-time PCR using a pair of primers directed against the 5'-end of luciferase mRNA.

The transcripts associated with polysomes were degraded at about the same rate as total cytoplasmic mRNA (data not shown). This suggests that even if there exist translated and untranslated pools of luciferase mRNA at any given time, the mRNA freely exchanges between them. This observation validates measurements of translational efficiency and rate of degradation.

Figure 7:
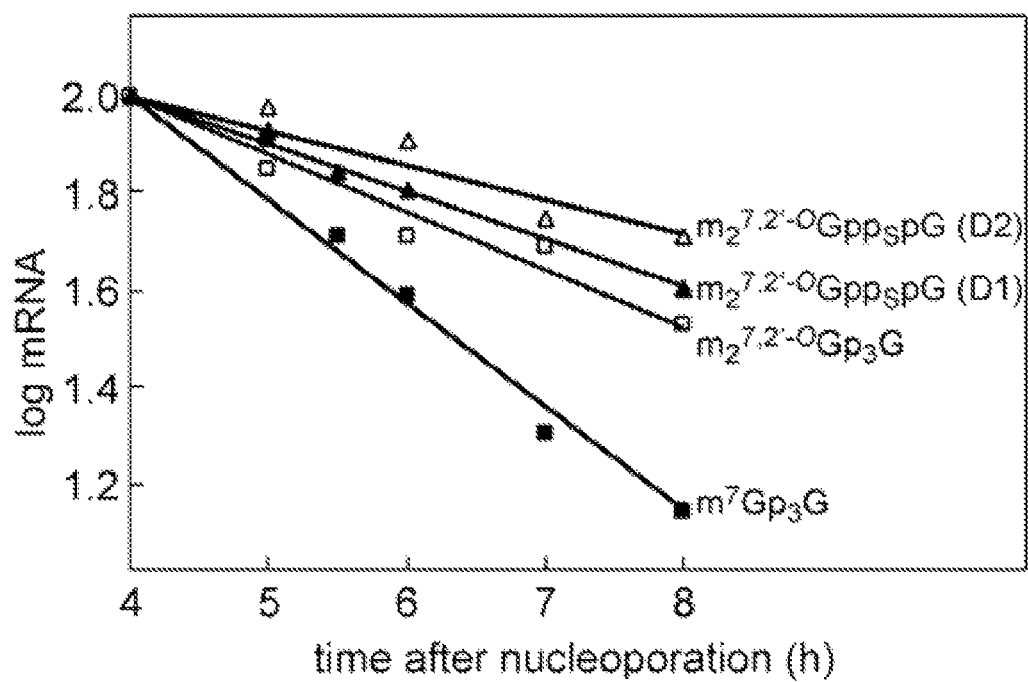
FIG. 7 depicts the decay of luciferase mRNAs capped with S-ARCAs in HC11 cells.

The stabilities of Luc-A$_{60}$ capped with various S-ARCAs were determined after nucleoporation into HC11 cells. The mRNA remaining in the cells at various times was determined by real-time PCR. Luc-$A_{60}$ capped with $m_2^{7,2'-O}Gpp_spG$ (D2) was more stable ($t_{1/2}$=257 min) than mRNA capped with either natural cap, $m^7Gp_3G$ ($t_{1/2}$=86 min), or the parent compound, $m_2^{7,2'-O}Gp_3G$ ($t_{1/1}$=155 min) (FIG. 7 and Table 2). This suggests that the increase in mRNAs stability resulted from resistance to hydrolysis by Dcp1/Dcp2. Neither $m_2^{7,2'-O}Gppp_sG$ (D1) ($t_{1/2}$=169 min) nor $m_2^{7,2'-O}Gpp_spG$ (D1) ($t_{1/2}$=185 min) conferred significantly greater stability than $m_2^{7,2'-O}Gp_3G$ ($t_{1/2}$=155 min) (Table 2). It was noteworthy that the affinity for eIF4E of both $m_2^{7,2'-O}Gppp_sG$ (D1) and $m_2^{7,2'-O}Gpp_spG$ (D1) was 3-fold higher than that of $m_2^{7,2'-O}Gp_3G$. One would have expected that mRNAs capped with these analogs would be more stable if the hypothesis about competition between eIF4E and Dcp1/Dcp2 were correct. See E. Grudzien et al., "Differential inhibition of mRNA degradation pathways by novel cap analogs," *J. Biol. Chem.*, vol. 281, pp. 1857-1867 (2006). We did not observe increases in either stability or translational efficiency (see below) for mRNAs capped with these analogs. This may indicate that, although $m_2^{7,2'-O}Gppp_sG$ (D1) and $m_2^{7,2'-O}Gpp_spG$ (D1) bound eIF4E more strongly, there was an upper limit beyond which high affinity for eIF4E did not accelerate overall translation. According to this interpretation, when the rate of cap binding becomes sufficiently high, some other step in protein synthesis initiation becomes rate limiting.

EXAMPLE 20

Translational Efficiency of Luciferase mRNAs Capped with S-ARCAs in HC11 Cells

We also determined the translational efficiency in cultured cells for luciferase mRNA capped with S-ARCAs. This involved two measurements conducted at various times following nucleoporation—luciferase activity measured by luminometry in cleared cell lysates, and Luc-$A_{60}$ levels measured by real-time PCR. Luciferase activity was normalized by the amount of luciferase mRNA that had been delivered into cells. To determine the amount of RNA present in the cells at a time immediately after nucleoporation, i.e., before any decay had occurred, cells were harvested at various times between 2 to 8 h post-nucleoporation, and cytoplasmic RNA was extracted. The amount of luciferase mRNA was measured by real time PCR using primers that amplify sequences near the 5'-end. Luciferase mRNA remaining at each time point was plotted as $log_{10}$ ([RNA]) versus time to determine $t_{1/2}$. The curve was extrapolated to 0 h, and the amount of RNA delivered into the cells was calculated. We defined conditions under which the accumulation of luciferase was linear with time, after an initial lag period of ~30 min for recruitment of mRNA to ribosomes, completing the first polypeptide chain, and release of luciferase into the cytosol.

Figure 8:
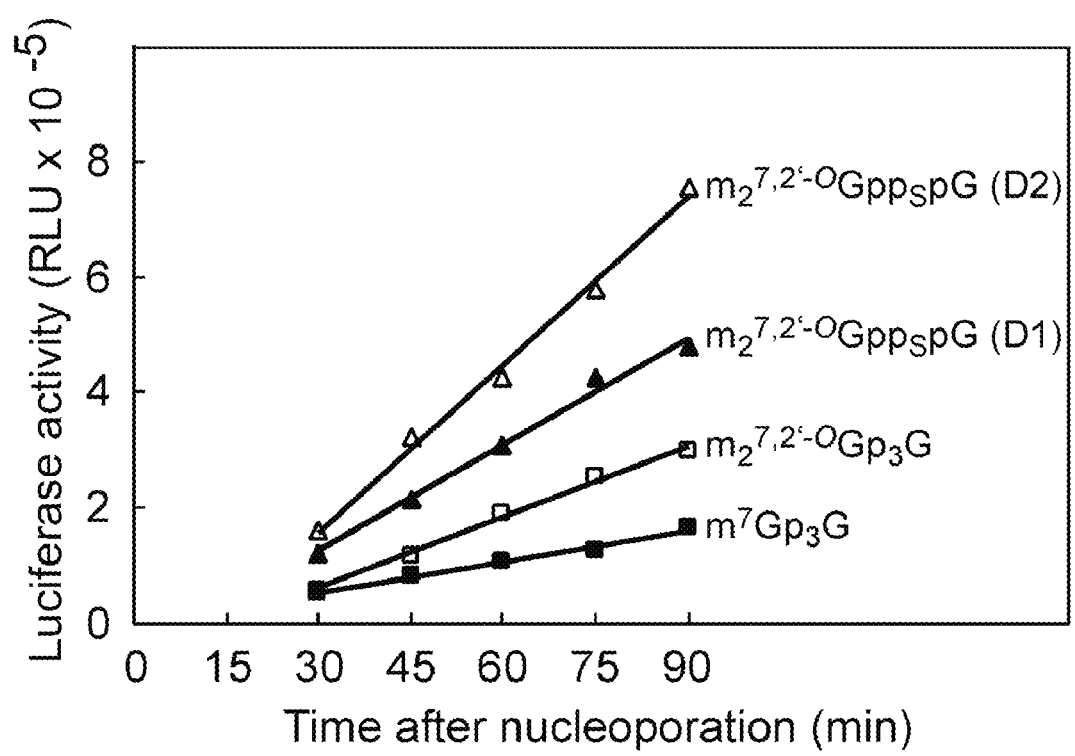
FIG. 8 depicts the translational efficiency of mRNAs capped with S-ARCAs in HC11 cells.

Luc-$A_{60}$ mRNA capped with $m_2^{7,2'-O}Gpp_spG$ (D1) and $m_2^{7,2'-O}Gpp_spG$ (D2) was translated 2.8- and 5.1-fold more efficiently than $m^7Gp_3G$-capped mRNA, respectively (FIG. 8 and Table 2). For cell-free translation in the rabbit reticulocyte lysate system, Luc-$A_{60}$ mRNAs capped with $m_2^{7,2'-O}Gpp_spG$ (D1) and $m_2^{7,2'-O}Gpp_spG$ (D2) were translated only 2.3-fold more efficiently than Luc-$A_{60}$ mRNA capped with $m^7Gp_3G$ (data not shown). This difference suggested that the increase in translational efficiency in cultured cells was related to higher mRNA stability (which is not a factor for cell-free translation systems), since only mRNA capped with analogs resistant to hDcp2 were translated more efficiently.

TABLE 2

Translational efficiency and stability of luciferase mRNAs with phosphorothioate cap analogs in HC11 cells.

| No. | Type of Cap on Luc-$A_{60}$ mRNA | Cap - eIF4E $K_{AS}$ [$M^{-6}$][a] | Dcp2 susceptibility[b] | mRNA half life (min)[c] | Relative translational efficiency[d] |
|---|---|---|---|---|---|
| 1 | $m^7Gp_3G$ | 9.4 ± 0.8 | ND | 86 ± 1* | 1.00 |
| 2 | $m_2^{7,2'-O}Gp_3G$ | 10.8 ± 0.3 | 100 | 155 ± 9 | 2.1 ± 0.2 |
| 3 | $m_2^{7,2'-O}Gppp_SG$ (D1) | 34.3 ± 1.3 | 96 | 169 ± 19 | 2.5 ± 0.8 |
| 4 | $m_2^{7,2'-O}Gppp_SG$ (D2) | 12.9 ± 0.9 | 98 | 164 ± 1 | 1.8 ± 0.4 |
| 5 | $m_2^{7,2'-O}Gpp_SpG$ (D1) | 42.1 ± 1.6 | 71 | 185 ± 22 | 2.8 ± 0.3 |
| 6 | $m_2^{7,2'-O}Gpp_SpG$ (D2) | 18.3 ± 3.4 | 6 | 257 ± 4* | 5.1 ± 0.5 |
| 7 | $m_2^{7,2'-O}Gp_SppG$ (D1) | 19.3 ± 1.8 | 84 | 149 ± 9 | 2.0 ± 0.1 |
| 8 | $m_2^{7,2'-O}Gp_SppG$ (D2) | 15.4 ± 0.5 | 91 | 139 ± 6 | 1.9 ± 0.1 |

[a]Equilibrium association constants for interaction of mouse eIF4E (amino acids 28-217) with various cap analogs at 20° C. Mouse eIF4E (residues 28-217) was expressed in *E. coli*, and fluorescence time-synchronized titrations were performed as described in J. Zuberek et al., "Phosphorylation of eIF4E attenuates its interaction with mRNA cap analogs by electrostatic repulsion: Intein-mediated protein ligation strategy to obtain phosphorylated protein," *RNA*, vol. 9, pp. 52-61 (2003) and A. Niedzwiecka et al., "Biophysical studies of eIF4E cap-binding protein: recognition of mRNA 5' cap structure and synthetic fragments of eIF4G and 4E-BP1 proteins," *J. Mol Biol*, vol. 319, pp. 615-635 (2002).
[b]The data of FIG. 4 were used to estimate susceptibility of oligonucleotides capped with various analogs to hDcp2 hydrolysis. The radioactivities in the peaks eluting at 44 min (undigested cap) and 38 min (pGp*) were corrected for background radioactivity and summed to represent total radioactivity in the cap. Dcp2 susceptibility is given by the radioactivity in pGp* expressed as a percentage of the total. (ND) Not determined.
[c]Degradation of 5'-terminal sequences in Luc-$A_{60}$ mRNAs capped with the indicated analogs was determined by real time PCR with primers directed against the 5'-end of luciferase mRNAs.
[d]Translational efficiency of Luc-$A_{60}$ mRNAs capped with indicated cap analogs in HC11 cells are shown. Luciferase activity was normalized by the amount of luciferase RNA in the cells. Relative translational efficiency was calculated as described by J. Jemielity et al., "Novel 'anti-reverse' cap analogues with superior translational properties" *RNA*, vol. 9, pp. 1108-1122 (2003).
*Half-lives that are significantly different (p < 0.05) from that of the $m_2^{7,2'-O}Gp_3G$-capped mRNA are indicated.

EXAMPLE 21

Luciferase mRNA Capped with S-ARCAs was More Efficiently Recruited to Polysomes in HC11 Cells We used an independent method to validate the observation that $m_2^{7,2'-O}Gpp_spG$-capped mRNAs were translated more efficiently, namely, their polysomal distribution (FIGS. 9A-9E). An increase in the rate of initiation relative to elongation or termination results in a shift of the mRNA from lighter to heavier polysomes. See H. Lodish, "Model for the regulation of mRNA translation applied to haemoglobin synthesis," Nature, vol. 251, pp. 385-388 (1974). The type of cap structure is not expected to affect the rate of elongation. Thus, a shift to higher polysomes indicates faster initiation.

Figure 9:
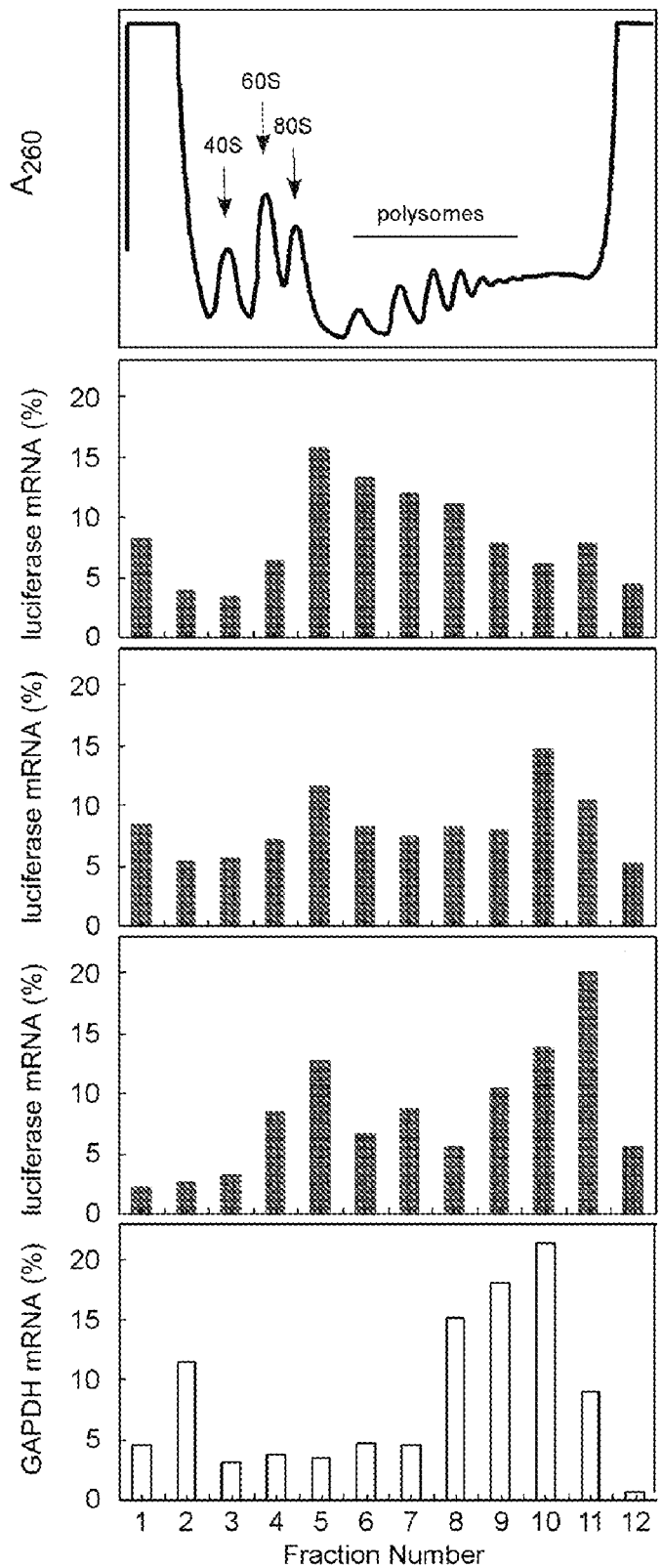
FIGS. 9A-9E depict the polysomal distribution of luciferase mRNA capped with S-ARCAs in HC11 cells, shown as sedimentation in sucrose gradients by monitoring by absorbance at 260 nm (A), and by use of real time PCR to show distribution of luciferase mRNA (B, C, and D) and GAPDH mRNA (E).

Luc $A_{60}$ mRNA capped with $m^7$ $Gp_3G$, $m_2^{7,2'-O}Gp_3G$ or $m_2^{7,2'-O}Gpp_spG$ (D2) was electroporated into HC11 cells. These cells were lysed 4 h after electroporation, and the cleared supernatants were layered on a sucrose gradient to separate polysomes from initiation complexes. Luciferase mRNA was predominantly present in polysomes (FIGS. 9A and 9B, fraction 6-11), although some also existed at the region of initiation complexes (fraction 3-5). Little luciferase mRNA was present in the untranslated messenger ribonucleoprotein complexes (mRNP) pool (FIGS. 9A and 9B, fraction 1-2). mRNA capped with a standard ARCA, $m_2^{7,2'-O}Gp_3G$, u was shifted to higher polysomes (FIG. 9C). However, mRNA capped with $m_2^{7,2'-O}Gpp_spG$ (D2) was shifted to even higher polysomes, and was simultaneously lost from the mRNP region (FIG. 9D). Under the same experimental conditions, endogenous GAPDH mRNA was efficiently translated (FIG. 9E), although some also sedimented in the region of initiation complexes. Overall, these results suggest that presence of $m_2^{7,2'-O}Gpp_spG$ (D2) at the 5'-end of luciferase transcripts increased their rate of initiation, confirming the results based on accumulation of luciferase activity.

EXAMPLE 22

Figure 10:
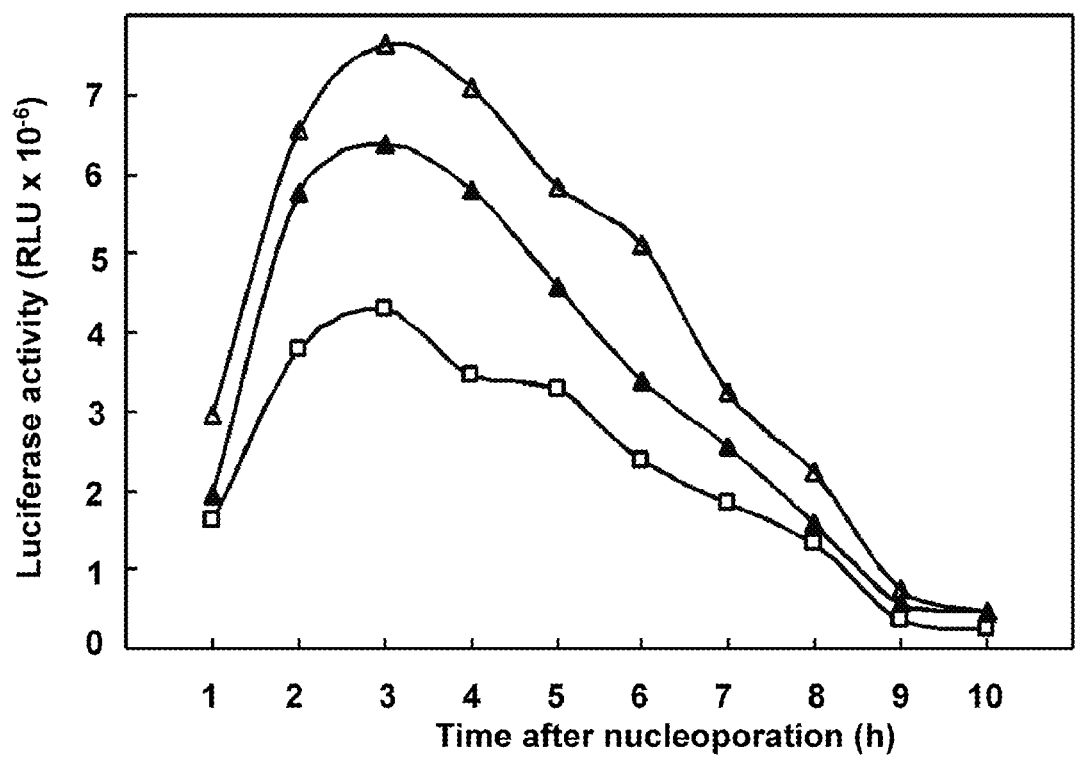
FIG. 10 depicts the time course of luciferase expression after nucleoporation of HC11 cells with S-ARCA-capped mRNAs.

The Combination of Greater Stability and Greater Translational Efficiency of S-ARCA Luciferase mRNA Produces More Overall Protein Expression in HC11 Cells We also determined the overall accumulation of luciferase, as measured by its enzymatic activity, as a function of time for mRNAs capped with $m_2^{7,2'-O}Gp_3G$, $m_2^{7,2'-O}Gpp_spG$ (D1), and $m_2^{7,2'-O}Gpp_spG$ (D2). HC11 cells were nucleoporated and then were lysed at various times up to 10 h. Luciferase activity measured in the supernatant was normalized for the amount of Luc-$A_{60}$ delivered into the cells. As shown in FIG. 10 luciferase activity in HC11 cells reached a maximum at 3 h, and then decreased 10-fold over 10 h. The kinetics of expression were consistent with the half-life of the luciferase protein, which is about 180 min (see J. Thompson et al., "Modulation of firefly luciferase stability and impact on studies of gene regulation," Gene, vol. 103, pp. 171-177 (1991)), and the half-life of the various luciferase mRNAs, which are 155, 185, and 257 min, respectively. The most luciferase accumulated for Luc-$A_{60}$ capped with $m_2^{7,2'-O}Gpp_spG$ (D2), which had both the highest translational efficiency and the greatest stability. The increase in overall protein expression from mRNAs capped with this analog is predicted to be even greater for proteins with longer half-lives.

EXAMPLE 23

Binding Affinities for eIF4E

The $K_{AS}$ values and free energies of binding ($\Delta G°$) of the S-analogs are presented in Table 3, together with the same data for their unmodified parent compounds. Surprisingly, not only does the presence of the phosphorothioate moiety fail to reduce binding affinity for eIF4E, but in some cases, affinity is significantly increased. The $K_{AS}$ values are strongly dependent both on the position of the phosphorothioate modification and on the absolute configuration around the asymmetric P-center. Interestingly, in each pair of diastereomers, the D1 member binds to eIF4E with an affinity that is 2.3- to 4.5-fold higher than the D2 member or the parent analog. For instance, $K_{AS}$ for the D1 isomer of $m_2^{7,2'-O}Gp_sppG$ is 3-fold higher than for D2 or $m_2^{7,2'-O}GpppG$. Similarly, $K_{AS}$ for the D1 isomer of $m_2^{7,2'-O}Gpp_spG$, is 2-fold higher than for D2 and 4.5-fold higher than for $m_2^{7,2'-O}GpppG$. The greatest differences in binding affinities between the D1/D2 diastereomers were observed for the γ-modified analogs. On the other hand, the greatest differences between modified and non-modified pairs were observed for β-substituted analogs.

TABLE 3

Equilibrium association constants ($K_{AS}$) and binding free energies ($\Delta G°$) for the binding of murine eIF4E (28-217) to phosphorothioate cap analogs, as determined by fluorescence quenching.

| | Cap Analog | $K_{AS}$ $\mu M^{-1}$ | $\Delta G°$ Kcal/mol |
|---|---|---|---|
| | $m^7GpppG$ | 9.4 ± 0.4 | −9.35 ± 0.02 |
| 1a | $m^7GpppsG$ (D1) | 23.6 ± 0.8 | −9.88 ± 0.02 |
| 1b | $m^7GpppsG$ (D2) | 13.1 ± 0.8 | −9.54 ± 0.03 |
| 2a | $m^7GppspG$ (D1) | 45.0 ± 1.1 | −10.26 ± 0.01 |
| 2b | $m^7GppspG$ (D2) | 23.0 ± 0.4 | −9.87 |
| 3a | $m^7GpspG$ (D1) | 30.8 ± 0.5 | −10.04 |
| 3b | $m^7GpspG$ (D2) | 10.0 ± 0.2 | −9.39 ± 0.01 |
| | $m^{7,2'-O}GpppG$ | 10.8 ± 0.3 | −9.43 |
| 4a | $m^{7,2'-O}GpppsG$ (D1) | 19.2 ± 0.8 | −9.76 |
| 4b | $m^{7,2'-O}GpppsG$ (D2) | 15.0 ± 0.6 | −9.62 |
| 5a | $m^{7,2'-O}GppspG$ (D1) | 43.1 ± 1.4 | −10.23 ± 0.02 |
| 5b | $m^{7,2'-O}GppspG$ (D2) | 19.3 ± 2.2 | −9.77 |
| 6a | $m^{7,2'-O}GpspG$ (D1) | 35.2 ± 1.1 | −10.12 |
| 6b | $M^{7,2'-O}GpsppG$ (D2) | 12.9 ± 0.4 | −9.53 |
| | $m^{7,2'-O}GppppG$ | 99.8 ± 6.0 | — |

** Determined for a diastereomeric mixture.

EXAMPLE 24

Susceptibility to Enzymatic Hydrolysis by Human and C. Elegans DcpS

The new series of S-analogs were subjected to in vitro enzymatic hydrolysis catalyzed by DcpS from both human and C. elegans sources. In all experiments, the corresponding unmodified cap analog was used as a positive control, i.e., $m^7GpppG$ for non-ARCA S-analogs and $m_2^{7,2'-O}GpppG$ for S-ARCAs. The amount of DcpS enzyme was optimized to provide complete degradation of the control substrate within 40-90 min. The samples collected from reaction mixtures at various time intervals were analyzed by RP HPLC (as described in Materials and Methods).

In Table 4, cap analogs at 4 μM concentration were subjected to enzymatic digestion by DcpS in conditions leading to complete degradation of the unmodified parent compound (i.e. $m^7GpppG$ for non-ARCA S-analogs and $m_2^{7,2'-O}GpppG$ for ARCAs) within 40-90 min. Samples collected from reaction mixtures at various time intervals were analysed by RP HPLC with UV detection at 260 nm as described in Materials and Methods. In Table 4, the analogs assigned as resistant remained completely undigested under the applied conditions, whereas the analogs assigned as hydrolyzed were hydrolyzed by DcpS with efficiency comparable to the respective unmodified parent compound. S-analogs modified at the γ-position were found to be resistant to hydrolysis, independent of the P-center absolute configuration (Table 4). The result was unchanged even if the reaction time was extended to 24 h, various amounts of enzyme were used, and composition of the reaction buffer was modified. All other S-analogs were hydrolyzed by hDcpS with efficiencies comparable to the unmodified parent analog. No significant differences were observed for S-analog hydrolysis by DcpS from human and *C. elegans* sources.

Analysis of the DcpS degradation products of analogs modified at the α-position allowed us to determine their absolute configuration around the asymmetric P-centers. We found that hydrolysis of either $m^7Gppp_sG$ (D1) or $m^7Gppp_sG$ (D2) by DcpS leads to $m^7GMP$ and either the D1 or D2 isomer of guanosine 5'-O-(1-thiodiphosphate) (GDPαS), whereas hydrolysis of either $m_2^{7,2'-O}Gppp_sG$ (D1) or $m_2^{7,2'-O}Gppp_sG$ (D2) leads to $m_2^{7,2'-O}GMP$ and either the D1 or D2 isomer of GDPαS (data not shown).

TABLE 4

Susceptibility of S-analogs to enzymatic hydrolysis by DcpS (from human and *C. elegans*) in vitro.
Resistance to enzymatic hydrolysis by DcpS (human and from *C. elegans*)

| | Cap Analog | |
|---|---|---|
| | $m^7GpppG$ | hydrolyzed |
| 1a | $m^7Gppp_sG$ (D1) | hydrolyzed |
| 1b | $m^7Gppp_sG$ (D2) | hydrolyzed |
| 2a | $m^7Gpp_spG$ (D1) | hydrolyzed |
| 2b | $m^7Gpp_spG$ (D2) | hydrolyzed |
| 3a | $m^7Gp_sppG$ (D1) | resistant |
| 3b | $m^7Gp_sppG$ (D2) | resistant |
| | $m_2^{7,2'-O}GpppG$ | hydrolyzed |
| 4a | $m_2^{7,2'-O}Gppp_sG$ (D1) | hydrolyzed |
| 4b | $m_2^{7,2'-O}Gppp_sG$ (D2) | hydrolyzed |
| 5a | $m_2^{7,2'-O}Gpp_spG$ (D1) | hydrolyzed |
| 5b | $m_2^{7,2'-O}Gpp_spG$ (D2) | hydrolyzed |
| 6a | $m_2^{7,2'-O}Gp_sppG$ (D1) | resistant |
| 6b | $m_2^{7,2'-O}Gp_sppG$ (D2) | resistant |

EXAMPLE 25

Cap Analogs as Inhibitors of Cap-Dependent Translation

The ability of the new S-analogs to inhibit cap-dependent translation was assayed in a rabbit reticulocyte lysate system programmed with natural rabbit globin mRNA. Of the 12 S-analogs, two were selected that were modified at the γ-position, $m^7Gp_sppG$ (D1) and $m^7Gp_sppG$ (D2) since they were found to be resistant towards DcpS and since they are potentially more stable in vivo. Data for inhibition of translation were fit with a theoretical curve that describes cap-dependent translation as a function of a competitive inhibitor of mRNA binding (Cai et al. 1999). This allowed us to determine $K_I$, the cap analog concentration at which cap-dependent translation is inhibited in 50% (Table 5). Both S-analogs were found to be better inhibitors of cap-dependent translation than $m^7GpppG$, which constitutes additional evidence that the phosphorothioate moiety generally stabilizes the cap-eIF4E interaction. Moreover, $m^7Gp_sppG$ (D1) was significantly more inhibitory than its D2 counterpart ($K_I$=4.1±0.2 µM versus $K_I$=12.1±3.2 µM), which is in agreement with its higher binding affinity for eIF4E ($K_{AS}$=30.8±0.5 versus $K_{AS}$=10.0±0.2).

TABLE 5

Inhibitory constants ($K_I$) for inhibition of cap-dependent translation by γ-modified S-analogs in a rabbit reticulocyte lysate translation system.

| | Cap Analog | $K_I$ µM$^{-1}$ |
|---|---|---|
| | $m^7GpppG$ | 17.1 ± 2.5 |
| 3a | $m^7Gp_sppG$ (D1) | 4.1 ± 0.2 |
| 3b | $m^7Gp_sppG$ (D2) | 12.1 ± 3.2 |

EXAMPLE 26 mRNA Fragments Capped with S-ARCA as in Vivo Inhibitors of Cap-Dependent Translation A future application of S-ARCAs, especially the triphosphates in which the phosphorothioate modification occurs in the γ (gamma) position such as Compounds 6a and 6b under Example 17, would be as inhibitors of cap-dependent translation. It is well documented that cap-dependent translation is up-regulated in cancer cells and that down-regulation of eIF4E reverses the malignant phenotype. Fragments resulting from 3'→5' degradation of capped mRNAs must be decapped when they reach a length of less than 25 nt before complete degradation to nucleotides can occur. Such fragments capped with triphosphate S-ARCAs containing the phosphorothioate modification in the γ (gamma) position are expected to be resistant to DcpS, similar to what was shown for the cap dinucleotides themselves (Table 4, above). They are therefore expected to accumulate in the cell and compete with normal mRNAs for recruitment to the translational machinery. We will introduce mRNAs or mRNA fragments capped with triphosphate S-ARCAs substituted in the γ position (Compounds 6a and 6b under Example 17) into cultured cells. We will then measure cap-dependent versus cap-independent translation using reporter constructs. We expect the former to be preferentially inhibited. It should be noted that the ARCA modification is necessary for correct orientation of these S-ARCAs upon incorporation into the mRNA, since otherwise the phosphorothioate moiety would not be in the correct position to render the mRNA fragment resistant to DcpS.

In a similar matter, we will analyze the tetraphosphate S-ARCAs as potential inhibitors of cap-dependent translation. We expect that tetraphosphates S-ARCAs, especially those containing a δ-phosphorothioate group, will not be hydrolyzed by DcpS under physiological conditions and will inhibits cap-dependent translation

EXAMPLE 27

The claims specify all combinations of phosphorothioate modification of triphosphate and tetraphosphate cap analog dinucleotides, similar to those listed below. A modification of the ribose moiety of $m^7Guo$ is 2'-deoxy, 3'-deoxy, arabinose, 2'-O-ethyl, and 3'-O-ethyl. A modification of the 7-substituents of G is methyl, ethyl, propyl, butyl, benzyl, substituted benzyl, naphthylmethyl, substituted naphthylmethyl, and other substituted or unsubstituted C1 to C10 aliphatic or aromatic groups. A modification of the guanine moiety is to use adenine, uridine, cytosine, or $m^7G$. These various modifications can be synthesized as disclosed in this application and adapted from methods otherwise known in the art, e.g., U.S. Patent Application Publication 2003/0194759.

| n | Compound | $Y_1$ | $Y_2$ | $Y_3$ | $Y_4$ |
|---|---|---|---|---|---|
| 1 | $m_2^{7,R}Gp_SppG$ | S | O | O | — |
| 1 | $m_2^{7,R}Gpp_SpG$ | O | S | O | — |
| 1 | $m_2^{7,R}Gpp_SpG$ | O | O | S | — |
| 1 | $m_2^{7,R}Gppp_SG$ | S | O | S | — |
| 1 | $m_2^{7,R}Gpp_Sp_SG$ | S | S | O | — |
| 1 | $m_2^{7,R}Gpp_Sp_SG$ | O | S | S | — |
| 1 | $m_2^{7,R}Gp_Sp_Sp_SG$ | S | S | S | — |
| 2 | $m_2^{7,R}Gp_SpppG$ | S | O | O | O |
| 2 | $m_2^{7,R}Gpp_SppG$ | O | S | O | O |
| 2 | $m_2^{7,R}Gpp_SppG$ | O | O | S | O |
| 2 | $m_2^{7,R}Gpp_SppG$ | O | O | O | S |
| 2 | $m_2^{7,R}Gp_Sp_SppG$ | S | S | O | O |
| 2 | $m_2^{7,R}Gp_Spp_SpG$ | S | O | S | O |
| 2 | $m_2^{7,R}Gppp_Sp_SG$ | S | O | O | S |
| 2 | $m_2^{7,R}Gpp_Sp_SpG$ | O | S | S | O |
| 2 | $m_2^{7,R}Gpp_Spp_SG$ | O | S | O | S |
| 2 | $m_2^{7,R}Gppp_Sp_SG$ | O | O | S | S |
| 2 | $m_2^{7,R}Gp_Sp_Sp_SpG$ | S | S | S | O |
| 2 | $m_2^{7,R}Gp_Spp_Sp_SG$ | S | S | O | S |
| 2 | $m_2^{7,R}Gpp_Sp_Sp_SG$ | S | O | S | S |
| 2 | $m_2^{7,R}Gpp_Sp_Sp_SG$ | O | S | S | S |
| 2 | $m_2^{7,R}Gp_Sp_Sp_Sp_SG$ | S | S | S | S |

The complete disclosures of all references cited in this specification are hereby incorporated by reference. Also incorporated by reference are the complete disclosures of the following publications of the inventors' own work, which is not prior art to the present application: J. Kowalska et al., "Synthesis and characterization of mRNA cap analogs containing phosphorothioate substitutions that bind tightly to eIF4E and are resistant to the decapping pyrophosphatase DcpS," RNA, vol. 14, pp. 1119-1131 (2008); E. Grudzien-Nogalska et al., "Phosphorothioate cap analogs stabilize mRNA and increase translational efficiency in mammalian cells," RNA, vol. 13, pp. 1745-1755 (2007); and E. Darzynkiewicz et al., "Methylene and phosphorothioate cap dinucleotides: useful tools to study decapping and translantion", an abstract and poster presented to the RNA Meeting, Seattle, Wash., Jun. 20-25, 2006. In the event of an otherwise irreconcilable conflict, however, the present specification shall control.

What is claimed:
1. A composition comprising

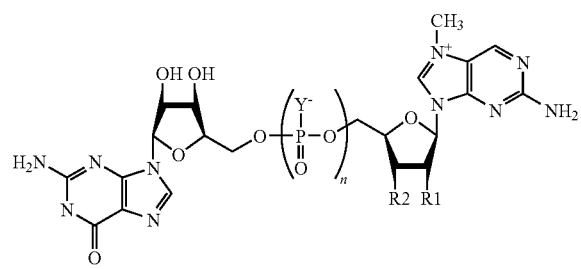

wherein:
Each Y is selected from the group consisting of O and S; the various Ys may be the same or different; and at least one Y is S;
R1 is selected from the group consisting of H, OH, $OCH_3$, and $OCH_2CH_3$;
R2 is selected from the group consisting of H, OH, $OCH_3$, and $OCH_2CH_3$;
n is 3 or 4; and
if R1 is OH, then R2 is not OH.

2. A composition as recited in claim 1, wherein said composition consists essentially of a single stereoisomer.

3. A composition as recited in claim 1, wherein said composition comprises a mixture of at least two diastereomers, a first diastereomer and a second diastereomer; wherein said first and second diastereomers are otherwise identical, except that said first and second diastereomers have different stereochemical configurations at a chiral phosphorus atom; wherein said chiral phosphorus atom is a phosphorus atom that is bound to a sulfur atom.

4. An RNA molecule whose 5' end incorporates a composition as recited in claim 1.

5. A method for synthesizing an RNA molecule as recited in claim 4 in vitro; said method comprising reacting ATP, CTP, UTP, GTP, a composition as recited, and a polynucleotide template; in the presence of an RNA polymerase; under conditions conducive to transcription by the RNA polymerase of the polynucleotide template into an RNA copy; whereby some of the RNA copies will incorporate the composition as recited to make an RNA molecule as recited.

6. A method for synthesizing a protein or peptide in vitro, said method comprising translating an RNA molecule as recited in claim 4 in a cell-free protein synthesis system, wherein the RNA molecule comprises an open reading frame, under conditions conducive to translating the open reading frame of the RNA molecule into the protein or peptide encoded by the open reading frame.

7. A method for synthesizing a protein or peptide in vivo, said method comprising introducing an RNA molecule as recited in claim 4 into cells, wherein the RNA molecule comprises an open reading frame, under conditions conducive to translating the open reading frame of the RNA molecule into the protein or peptide encoded by the open reading frame.

8. A composition as recited in claim 1; wherein n is 3 and said composition contains a β-phosphorothioate group, or wherein n is 4 and said composition contains a γ-phosphorothioate group; and wherein said composition is not hydrolyzed by Dcp2 under physiological conditions.

9. A composition as recited in claim 1; wherein n is 3 and said composition contains a γ-phosphorothioate group; or wherein n is 4 and said composition contains a δ-phosphorothioate group; and wherein said composition is not hydrolyzed by DcpS under physiological conditions, and said composition inhibits cap-dependent translation.

10. A method for synthesizing a protein or peptide in vivo; said method comprising introducing into cells an RNA molecule whose 5' end incorporates a composition as recited in claim 8, wherein the RNA molecule comprises an open reading frame; under conditions conducive to translating the open reading frame of the RNA molecule into the protein or peptide encoded by the open reading frame; wherein the in vivo protein expression is higher than the in vivo protein expression that would be obtained from an otherwise-identical method in which each Y is an oxygen atom, and in which no Y is a sulfur atom.

11. A composition comprising

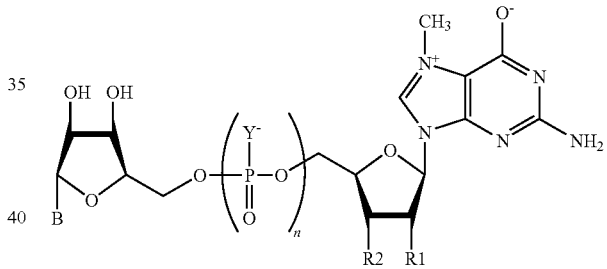

wherein:
Each Y is selected from the group consisting of O and S; the various Ys may be the same or different; and at least one Y is S;
R1 is selected from the group consisting of H, OH, $OCH_3$, and $OCH_2CH_3$;
R2 is selected from the group consisting of H, OH, $OCH_3$, and $OCH_2CH_3$;
n is 3 or 4; and
if R1 is OH, then R2 is not OH;
and B is selected from the group consisting of

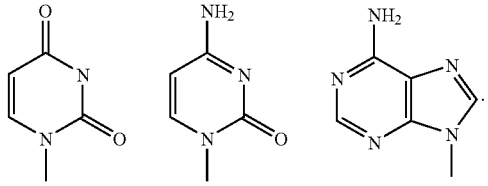

12. A composition as recited in claim 11, wherein said composition consists essentially of a single stereoisomer.

13. A composition as recited in claim 11, wherein said composition comprises a mixture of at least two diastereomers, a first diastereomer and a second diastereomer; wherein said first and second diastereomers are otherwise identical, except that said first and second diastereomers have different stereochemical configurations at a chiral phosphorus atom; wherein said chiral phosphorus atom is a phosphorus atom that is bound to a sulfur atom.

14. An RNA molecule whose 5' end incorporates a composition as recited in claim 11.

15. A method for synthesizing an RNA molecule as recited in claim 14 in vitro; said method comprising reacting ATP, CTP, UTP, GTP, a composition as recited, and a polynucleotide template; in the presence of an RNA polymerase; under conditions conducive to transcription by the RNA polymerase of the polynucleotide template into an RNA copy; whereby some of the RNA copies will incorporate the composition as recited to make an RNA molecule as recited.

16. A method for synthesizing a protein or peptide in vitro, said method comprisng translating an RNA molecule as recited in claim 14 in a cell-free protein synthesis system, wherein the RNA molecule comprises an open reading frame, under conditions conducive to translating the open reading frame of the RNA molecule into the protein or peptide encoded by the open reading frame.

17. A method for synthesizing a protein or peptide in vivo, said method comprising introducing an RNA molecule as recited in claim 14 into cells, wherein the RNA molecule comprises an open reading frame, under conditions conducive to translating the open reading frame of the RNA molecule into the protein or peptide encoded by the open reading frame.

18. A composition as recited in claim 11; wherein n is 3 and said composition contains a β-phosphorothioate group, or wherein n is 4 and said composition contains a γ-phosphorothioate group; and wherein said composition is not hydrolyzed by Dcp2 under physiological conditions.

19. A composition as recited in claim 11; wherein n is 3 and said composition contains a γ-phosphorothioate group; or wherein n is 4 and said composition contains a δ-phosphorothioate group; and wherein said composition is not hydrolyzed by DcpS under physiological conditions, and said composition inhibits cap-dependent translation.

20. A method for synthesizing a protein or peptide in vivo; said method comprising introducing into cells an RNA molecule whose 5' end incorporates a composition as recited in claim 17, wherein the RNA molecule comprises an open reading frame; under conditions conducive to translating the open reading frame of the RNA molecule into the protein or peptide encoded by the open reading frame; wherein the in vivo protein expression is higher than the in vivo protein expression that would be obtained from an otherwise-identical method in which each Y is an oxygen atom, and in which no Y is a sulfur atom.

21. A composition comprising

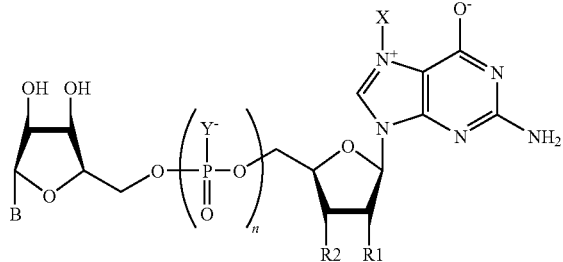

wherein:
Each Y is selected from the group consisting of O and S; the various Ys may be the same or different; and at least one Y is S;

R1 is selected from the group consisting of H, OH, OCH$_3$, and OCH$_2$CH$_3$;
R2 is selected from the group consisting of H, OH, OCH$_3$, and OCH$_2$CH$_3$;
n is 3 or 4; and
if R1 is OH, then R2 is not OH; and
B is selected from the group consisting of guanine, adenine, uridine, cytosine;
and X is selected from the group consisting of methyl, ethyl, propyl, butyl, benzyl, substituted benzyl, naphthylmethyl, substituted naphthylmethyl, and other substituted and unsubstituted C1 to C10 aliphatic or aromatic groups.

22. A composition as recited in claim 21, wherein said composition consists essentially of a single stereoisomer.

23. A composition as recited in claim 21, wherein said composition comprises a mixture of at least two diastereomers, a first diastereomer and a second diastereomer; wherein said first and second diastereomers are otherwise identical, except that said first and second diastereomers have different stereochemical configurations at a chiral phosphorus atom; wherein said chiral phosphorus atom is a phosphorus atom that is bound to a sulfur atom.

24. An RNA molecule whose 5' end incorporates a composition as recited in claim 21.

25. A method for synthesizing an RNA molecule as recited in claim 24 in vitro; said method comprising reacting ATP, CTP, UTP, GTP, a composition as recited, and a polynucleotide template; in the presence of an RNA polymerase; under conditions conducive to transcription by the RNA polymerase of the polynucleotide template into an RNA copy; whereby some of the RNA copies will incorporate the composition as recited to make an RNA molecule as recited.

26. A method for synthesizing a protein or peptide in vitro, said method comprising translating an RNA molecule as recited in claim 24 in a cell-free protein synthesis system, wherein the RNA molecule comprises an open reading frame, under conditions conducive to translating the open reading frame of the RNA molecule into the protein or peptide encoded by the open reading frame.

27. A method for synthesizing a protein or peptide in vivo, said method comprising introducing an RNA molecule as recited in claim 24 into cells, wherein the RNA molecule comprises an open reading frame, under conditions conducive to translating the open reading frame of the RNA molecule into the protein or peptide encoded by the open reading frame.

28. A composition as recited in claim 21; wherein n is 3 and said composition contains a β-phosphorothioate group, or wherein n is 4 and said composition contains a γ-phosphorothioate group; and wherein said composition is not hydrolyzed by Dcp2 under physiological conditions.

29. A composition as recited in claim 21; wherein n is 3 and said composition contains a γ-phosphorothioate group; or wherein n is 4 and said composition contains a δ-phosphorothioate group; and wherein said composition is not hydrolyzed by DcpS under physiological conditions, and said composition inhibits cap-dependent translation.

30. A method for synthesizing a protein or peptide in vivo; said method comprising introducing into cells an RNA molecule whose 5' end incorporates a composition as recited in claim 28, wherein the RNA molecule comprises an open reading frame; under conditions conducive to translating the open reading frame of the RNA molecule into the protein or peptide encoded by the open reading frame; wherein the in vivo protein expression is higher than the in vivo protein expression that would be obtained from an otherwise-identical method in which each Y is an oxygen atom, and in which no Y is a sulfur atom.

31. A composition comprising

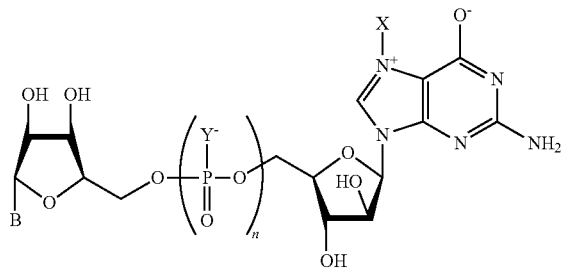

wherein:
Each Y is selected from the group consisting of O and S; the various Ys may be the same or different; and at least one Y is S;
n is 3 or 4;
B is selected from the group consisting of guanine, adenine, uridine, cytosine;
and X is selected from the group consisting of methyl, ethyl, propyl, butyl, benzyl, substituted benzyl, naphthylmethyl, substituted naphthylmethyl, and substituted or unsubstituted C1 to C10 aliphatic or aromatic groups.

32. A composition as recited in claim 31, wherein said composition consists essentially of a single stereoisomer.

33. A composition as recited in claim 31, wherein said composition comprises a mixture of at least two diastereomers, a first diastereomer and a second diastereomer; wherein said first and second diastereomers are otherwise identical, except that said first and second diastereomers have different stereochemical configurations at a chiral phosphorus atom; wherein said chiral phosphorus atom is a phosphorus atom that is bound to a sulfur atom.

34. An RNA molecule whose 5' end incorporates a composition as recited in claim 31.

35. A method for synthesizing an RNA molecule as recited in claim 34 in vitro; said method comprising reacting ATP, CTP, UTP, GTP, a composition as recited, and a polynucleotide template; in the presence of an RNA polymerase; under conditions conducive to transcription by the RNA polymerase of the polynucleotide template into an RNA copy; whereby some of the RNA copies will incorporate the composition as recited to make an RNA molecule as recited.

36. A method for synthesizing a protein or peptide in vitro, said method comprising translating an RNA molecule as recited in claim 34 in a cell-free protein synthesis system, wherein the RNA molecule comprises an open reading frame, under conditions conducive to translating the open reading frame of the RNA molecule into the protein or peptide encoded by the open reading frame.

37. A method for synthesizing a protein or peptide in vivo, said method comprising introducing an RNA molecule as recited in claim 34 into cells, wherein the RNA molecule comprises an open reading frame, under conditions conducive to translating the open reading frame of the RNA molecule into the protein or peptide encoded by the open reading frame.

38. A composition as recited in claim 31; wherein n is 3 and said composition contains a β-phosphorothioate group, or wherein n is 4 and said composition contains a γ-phosphorothioate group; and wherein said composition is not hydrolyzed by Dcp2 under physiological conditions.

39. A composition as recited in claim 31; wherein n is 3 and said composition contains a γ-phosphorothioate group; or wherein n is 4 and said composition contains a δ-phosphorothioate group; and wherein said composition is not hydrolyzed by DcpS under physiological conditions, and said composition inhibits cap-dependent translation.

40. A method for synthesizing a protein or peptide in vivo; said method comprising introducing into cells an RNA molecule whose 5' end incorporates a composition as recited in claim 38, wherein the RNA molecule comprises an open reading frame; under conditions conducive to translating the open reading frame of the RNA molecule into the protein or peptide encoded by the open reading frame; wherein the in vivo protein expression is higher than the in vivo protein expression that would be obtained from an otherwise-identical method in which each Y is an oxygen atom, and in which no Y is a sulfur atom.

41. A composition comprising

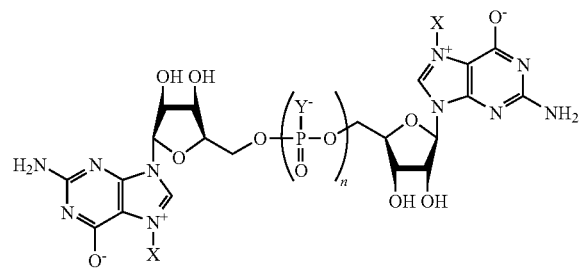

wherein:
Each Y is selected from the group consisting of O and S; the various Ys may be the same or different; and at least one Y is S; and
n is 3 or 4; and
X is selected from the group consisting of methyl, ethyl, propyl, butyl, benzyl, substituted benzyl, naphthylmethyl, substituted naphthylmethyl, and substituted or unsubstituted C1 to C10 aliphatic or aromatic groups; the various X's may be the same or different.

42. A composition as recited in claim 41, wherein said composition consists essentially of a single stereoisomer.

43. A composition as recited in claim 41, wherein said composition comprises a mixture of at least two diastereomers, a first diastereomer and a second diastereomer; wherein said first and second diastereomers are otherwise identical, except that said first and second diastereomers have different stereochemical configurations at a chiral phosphorus atom; wherein said chiral phosphorus atom is a phosphorus atom that is bound to a sulfur atom.

44. An RNA molecule whose 5' end incorporates a composition as recited in claim 41.

45. A method for synthesizing an RNA molecule as recited in claim 44 in vitro; said method comprising reacting ATP, CTP, UTP, GTP, a composition as recited, and a polynucleotide template; in the presence of an RNA polymerase; under conditions conducive to transcription by the RNA polymerase of the polynucleotide template into an RNA copy; whereby some of the RNA copies will incorporate the composition as recited to make an RNA molecule as recited.

46. A method for synthesizing a protein or peptide in vitro, said method comprising translating an RNA molecule as recited in claim 44 in a cell-free protein synthesis system, wherein the RNA molecule comprises an open reading frame, under conditions conducive to translating the open reading frame of the RNA molecule into the protein or peptide encoded by the open reading frame.

47. A method for synthesizing a protein or peptide in vivo, said method comprising introducing an RNA molecule as recited in claim 44 into cells, wherein the RNA molecule comprises an open reading frame, under conditions conducive to translating the open reading frame of the RNA molecule into the protein or peptide encoded by the open reading frame.

48. A composition as recited in claim 41; wherein n is 3 and said composition contains a β-phosphorothioate group, or wherein n is 4 and said composition contains a γ-phosphorothioate group; and wherein said composition is not hydrolyzed by Dcp2 under physiological conditions.

49. A composition as recited in claim 41; wherein n is 3 and said composition contains a γ-phosphorothioate group; or wherein n is 4 and said composition contains a δ-phosphorothioate group; and wherein said composition is not hydrolyzed by DcpS under physiological conditions, and said composition inhibits cap-dependent translation.

50. A method for synthesizing a protein or peptide in vivo; said method comprising introducing into cells an RNA molecule whose 5' end incorporates a composition as recited in claim 48, wherein the RNA molecule comprises an open reading frame; under conditions conducive to translating the open reading frame of the RNA molecule into the protein or peptide encoded by the open reading frame; wherein the in vivo protein expression is higher than the in vivo protein expression that would be obtained from an otherwise-identical method in which each Y is an oxygen atom, and in which no Y is a sulfur atom.

51. A composition comprising

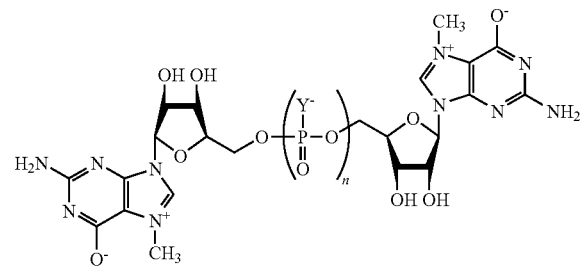

wherein:
Each Y is selected from the group consisting of O and S; the various Ys may be the same or different; and at least one Y is S; and
n is 3 or 4.

52. A composition as recited in claim 51, wherein said composition consists essentially of a single stereoisomer.

53. A composition as recited in claim 51, wherein said composition comprises a mixture of at least two diastereomers, a first diastereomer and a second diastereomer; wherein said first and second diastereomers are otherwise identical, except that said first and second diastereomers have different stereochemical configurations at a chiral phosphorus atom; wherein said chiral phosphorus atom is a phosphorus atom that is bound to a sulfur atom.

54. An RNA molecule whose 5' end incorporates a composition as recited in claim 51.

55. A method for synthesizing an RNA molecule as recited in claim 54 in vitro; said method comprising reacting ATP, CTP, UTP, GTP, a composition as recited, and a polynucleotide template; in the presence of an RNA polymerase; under conditions conducive to transcription by the RNA polymerase of the polynucleotide template into an RNA copy; whereby some of the RNA copies will incorporate the composition as recited to make an RNA molecule as recited.

56. A method for synthesizing a protein or peptide in vitro, said method comprising translating an RNA molecule as recited in claim 54 in a cell-free protein synthesis system, wherein the RNA molecule comprises an open reading frame, under conditions conducive to translating the open reading frame of the RNA molecule into the protein or peptide encoded by the open reading frame.

57. A method for synthesizing a protein or peptide in vivo, said method comprising introducing an RNA molecule as recited in claim 54 into cells, wherein the RNA molecule comprises an open reading frame, under conditions conducive to translating the open reading frame of the RNA molecule into the protein or peptide encoded by the open reading frame.

58. A composition as recited in claim 51; wherein n is 3 and said composition contains a β-phosphorothioate group, or wherein n is 4 and said composition contains a γ-phosphorothioate group; and wherein said composition is not hydrolyzed by Dcp2 under physiological conditions.

59. A composition as recited in claim 51; wherein n is 3 and said composition contains a γ-phosphorothioate group; or wherein n is 4 and said composition contains a δ-phosphorothioate group; and wherein said composition is not hydrolyzed by DcpS under physiological conditions, and said composition inhibits cap-dependent translation.

60. A method for synthesizing a protein or peptide in vivo; said method comprising introducing into cells an RNA molecule whose 5' end incorporates a composition as recited in claim 58, wherein the RNA molecule comprises an open reading frame; under conditions conducive to translating the open reading frame of the RNA molecule into the protein or peptide encoded by the open reading frame; wherein the in vivo protein expression is higher than the in vivo protein expression that would be obtained from an otherwise-identical method in which each Y is an oxygen atom, and in which no Y is a sulfur atom.

61. A composition comprising one or more compounds selected from the group consisting of
$m_2^{7,2'-O}Gpp_spG$; $m_2^{7,3'-O}Gpp_spG$; $m_2^{7,2'-O}Gppp_spG$; $m_2^{7,3'-O}Gppp_spG$; $m_2^{7,2'-O}Gpp_sppG$; $m_2^{7,3'-O}Gpp_sppG$; $m_2^{7,2'-O}Gp_sp_spG$; $m_2^{7,3'-O}Gp_sp_spG$; $m_2^{7,2'-O}Gpp_sp_sG$; $m_2^{7,3'-O}Gpp_sp_sG$; $bn^7m^{2'-O}Gpp_spG$; $bn^7m^{3'-O}Gpp_spG$; $bn^7m^{2'-O}Gppp_spG$; $bn^7m^{3'-O}Gppp_spG$; $bn^7m^{2'-O}Gpp_sppG$; $bn^7m^{3'-O}Gpp_sppG$; $bn^7m^{2'-O}Gp_sp_spG$; $bn^7m^{3'-O}Gp_sp_spG$; $bn^7m^{2'-O}Gpp_sp_sG$; and $bn^7m^{3'-O}Gpp_sp_sG$.

62. A composition as recited in claim 61, wherein said composition consists essentially of a single stereoisomer of one of said compounds.

63. A composition as recited in claim 61, wherein said composition comprises a mixture of at least two diastereomers of one of said compounds, a first diastereomer and a second diastereomer; wherein said first and second diastereomers are otherwise identical, except that said first and second diastereomers have different stereochemical configurations at a chiral phosphorus atom; wherein said chiral phosphorus atom is a phosphorus atom that is bound to a sulfur atom.

64. An RNA molecule whose 5' end incorporates a composition as recited in claim 61.

65. A method for synthesizing an RNA molecule as recited in claim 64 in vitro; said method comprising reacting ATP, CTP, UTP, GTP, a composition as recited, and a polynucleotide template; in the presence of an RNA polymerase; under conditions conducive to transcription by the RNA polymerase of the polynucleotide template into an RNA copy; whereby some of the RNA copies will incorporate the composition as recited to make an RNA molecule as recited.

66. A method for synthesizing a protein or peptide in vitro, said method comprising translating an RNA molecule as recited in claim 64 in a cell-free protein synthesis system, wherein the RNA molecule comprises an open reading frame, under conditions conducive to translating the open reading frame of the RNA molecule into the protein or peptide encoded by the open reading frame.

67. A method for synthesizing a protein or peptide in vivo, said method comprising introducing an RNA molecule as recited in claim 64 into cells, wherein the RNA molecule comprises an open reading frame, under conditions conducive to translating the open reading frame of the RNA molecule into the protein or peptide encoded by the open reading frame.

* * * * *

UNITED STATES PATENT AND TRADEMARK OFFICE
CERTIFICATE OF CORRECTION

PATENT NO.      : 8,153,773 B2
APPLICATION NO. : 12/280282
DATED           : April 10, 2012
INVENTOR(S)     : Jacek Jemielity et al.

It is certified that error appears in the above-identified patent and that said Letters Patent is hereby corrected as shown below:

Title Page 2, Item (56) left column, in the Darzynkiewicz *et al.* (1988) citation, replace "m7G, m22.7G or m32.2.7G" with --$m^7G$, $m_2^{2,7}G$ or $m_3^{2,2,7}G$--

Col. 2, line 19, replace "$m_2^{2,7}G$ or $M_3^{2,2,7}G$" with --$m_2^{2,7}G$ or $m_3^{2,2,7}G$--

Col. 4, line 20, replace "neither in vitro nor" with --in vitro or--

Col. 4, line 66, replace "counterpart]." with --counterpart.--

Col. 5, line 42, replace "DEAD" with --DEAE--

Col. 5, line 57, replace "m/min" with --ml/min--

Col. 8, line 5, replace "if" with --in--

Col. 11, line 8, replace "mL" with --ml--

Col. 11, line 11, replace "mL" with --ml--

Col. 12, line 29, replace "In case of" with --For--

Col. 12, line 58, replace "subunits and initiation complexes," with --subunits, initiation complexes, and polysomes,--

Col. 14, line 22, replace "m3(2.2.7)GpppG" with --$m_3^{2,2,7}GpppG$--

Col. 17, line 40, delete "either of"

Col. 18, line 12, replace "$m_2^{7,3'-O}G$" with --$m_2^{7,3'-O}Gpp_{CH2}pG$--

Signed and Sealed this
Twenty-first Day of August, 2012

David J. Kappos
*Director of the United States Patent and Trademark Office*

CERTIFICATE OF CORRECTION (continued)
U.S. Pat. No. 8,153,773 B2

Col. 19, line 4, replace "$t_{1/1}$" with --$t_{1/2}$--

Col. 21, line 25, delete the lone letter "u" at the end of the line

Col. 22, line 40, delete "**Determined for a diastereomeric mixture."

Col. 29, Claim 18, line 33, replace "Dcp2under" with --Dcp2 under--

UNITED STATES PATENT AND TRADEMARK OFFICE
CERTIFICATE OF CORRECTION

Page 1 of 1

PATENT NO. : 8,153,773 B2
APPLICATION NO. : 12/280282
DATED : April 10, 2012
INVENTOR(S) : Jacek Jemielity et al.

It is certified that error appears in the above-identified patent and that said Letters Patent is hereby corrected as shown below:

In the Claims

In Claim 1, Column 27, beginning at Line 13 and ending at Line 23, replace the following structure:

"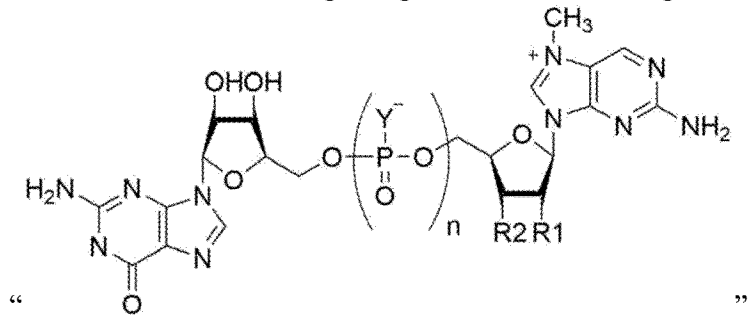"

With:

--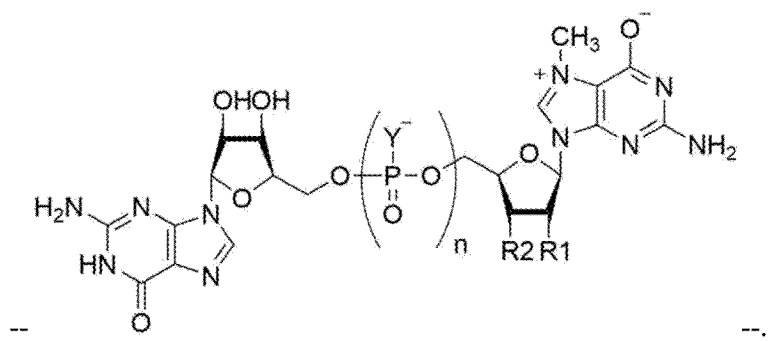--.

Signed and Sealed this
Twenty-sixth Day of May, 2020

Andrei Iancu
*Director of the United States Patent and Trademark Office*

SEQUENCE LISTING

```
<160> NUMBER OF SEQ ID NOS: 4

<210> SEQ ID NO 1
<211> LENGTH: 20
<212> TYPE: PRT
<213> ORGANISM: Artificial Sequence
<220> FEATURE:
<223> OTHER INFORMATION: Hecate.

<400> SEQUENCE: 1

Cys Gly Thr Thr Cys Gly Gly Thr Thr Gly Gly Cys Ala Gly Ala Ala
1               5                   10                  15

Gly Cys Thr Ala
            20

<210> SEQ ID NO 2
<211> LENGTH: 24
<212> TYPE: DNA
<213> ORGANISM: Artificial Sequence
<220> FEATURE:
<223> OTHER INFORMATION: Codon-optimized hecate coding sequence.

<400> SEQUENCE: 2
actgttgagc aattcacgtt catt                                              24

<210> SEQ ID NO 3
<211> LENGTH: 21
<212> TYPE: DNA
<213> ORGANISM: Artificial Sequence
<220> FEATURE:
<223> OTHER INFORMATION: Additional DNA sequence added to 5' end of
      hecate coding sequence.

<400> SEQUENCE: 3
caatgtgtcc gtcgtggatc t                                                 21

<210> SEQ ID NO 4
<211> LENGTH: 22
<212> TYPE: DNA
<213> ORGANISM: Artificial Sequence
```

```
<220> FEATURE:
<223> OTHER INFORMATION: Additional DNA sequence added to the 3' end of
      the hecate coding sequence.

<400> SEQUENCE: 4
gaagagtggg agttgctgtt ga                                              22
```